(12) United States Patent
Kim-Whitty

(10) Patent No.: US 10,888,228 B2
(45) Date of Patent: *Jan. 12, 2021

(54) METHOD AND SYSTEM FOR CORRELATING ANATOMY USING AN ELECTRONIC MOBILE DEVICE TRANSPARENT DISPLAY SCREEN

(71) Applicant: SK COMMERCIAL CONSTRUCTION, INC., Belton, TX (US)

(72) Inventor: Suk K. Kim-Whitty, Belton, TX (US)

( * ) Notice: Subject to any disclaimer, the term of this patent is extended or adjusted under 35 U.S.C. 154(b) by 369 days.

This patent is subject to a terminal disclaimer.

(21) Appl. No.: 15/901,016

(22) Filed: Feb. 21, 2018

(65) Prior Publication Data
US 2018/0177403 A1 Jun. 28, 2018

Related U.S. Application Data

(63) Continuation-in-part of application No. 15/631,981, filed on Jun. 23, 2017, now abandoned, which is a
(Continued)

(51) Int. Cl.
*A61B 5/00* (2006.01)
*A61B 90/00* (2016.01)
(Continued)

(52) U.S. Cl.
CPC .......... *A61B 5/0075* (2013.01); *A61B 5/0035* (2013.01); *A61B 5/055* (2013.01);
(Continued)

(58) Field of Classification Search
CPC ........ A61B 2090/364; A61B 2090/365; A61B 2090/373; A61B 2090/374; A61B 2090/376; A61B 5/0035; A61B 5/0075; A61B 5/055; A61B 5/4504; A61B 6/12; A61B 6/4477; A61B 6/462; A61B 6/505; A61B 6/5229; A61B 90/361; A61B 90/39; G06T 2207/10088; G06T 2207/10116;
(Continued)

(56) References Cited

U.S. PATENT DOCUMENTS 9,367,093 B2 * 6/2016 Pance .................. G06F 1/1647
9,801,693 B1 * 10/2017 Kim-Whitty ........ H05K 999/99

* cited by examiner

*Primary Examiner* — Michael T Rozanski
(74) *Attorney, Agent, or Firm* — Hulsey P.C.

(57) ABSTRACT

Method and system form a correlated view of human or other animal anatomy using at least one transparent display screen associated with an electronic mobile device. The view relates an optical view with other electromagnetic spectrum images with a non-optical electromagnetic image of selected portions of human or other animal anatomy. At least three visible position markers associate with selected positions of a predetermined portion of human or other animal anatomy. The disclosure forms a correlated view of the predetermined portion of human or other animal anatomy by relating said at least one non-optical electromagnetic image of the at least three visible position markers with a visual image of said at least three visible position markers. The view correlates the size and dimensions of the optical view and non-optical electromagnetic image of the predetermined portion of human or other animal anatomy.

31 Claims, 9 Drawing Sheets

Related U.S. Application Data continuation-in-part of application No. 15/464,231, filed on Mar. 20, 2017, now abandoned, and a continuation-in-part of application No. 15/477,124, filed on Apr. 3, 2017, now Pat. No. 9,967,553, and a continuation-in-part of application No. 15/477,301, filed on Apr. 3, 2017, now Pat. No. 10,116,924, and a continuation-in-part of application No. 15/477,131, filed on Apr. 3, 2017, now Pat. No. 9,801,693.

(60) Provisional application No. 62/420,544, filed on Nov. 10, 2016.

(51) Int. Cl.
*A61B 5/055* (2006.01)
*G06T 7/33* (2017.01)
*A61B 6/00* (2006.01)
*A61B 6/12* (2006.01)

(52) U.S. Cl.
CPC .............. *A61B 5/4504* (2013.01); *A61B 6/12* (2013.01); *A61B 6/462* (2013.01); *A61B 6/505* (2013.01); *A61B 6/5229* (2013.01); *A61B 90/39* (2016.02); *G06T 7/337* (2017.01); *A61B 6/4417* (2013.01); *A61B 90/361* (2016.02); *A61B 2090/364* (2016.02); *A61B 2090/365* (2016.02); *A61B 2090/373* (2016.02); *A61B 2090/374* (2016.02); *A61B 2090/376* (2016.02); *G06T 2207/10088* (2013.01); *G06T 2207/10116* (2013.01); *G06T 2207/30008* (2013.01); *G06T 2207/30204* (2013.01)

(58) Field of Classification Search
CPC . G06T 2207/30008; G06T 2207/30204; G06T 7/337
See application file for complete search history.

METHOD AND SYSTEM FOR CORRELATING ANATOMY USING AN ELECTRONIC MOBILE DEVICE TRANSPARENT DISPLAY SCREEN

CROSS REFERENCE TO RELATED APPLICATIONS

This application further claims the benefit of the following non-provisional applications, all of which are here expressly incorporated by reference:

This application is a Continuation in part of U.S. patent application Ser. No. 15/631,981, filed on Jun. 6, 2017, entitled, "Method And System For Correlating Anatomy Using An Electronic Mobile Device Transparent Display Screen," now abandoned, which is a Continuation-in-part of U.S. patent application Ser. No. 15/477,124, filed on Apr. 3, 2017, "Enhanced Transparent Display Screen For Mobile Device And Methods Of Operation," filed on Apr. 3, 2017, now U.S. Pat. No. 9,967,553, issued on May 8, 2018, which is a Continuation-in-part of U.S. patent application Ser. No. 15/477,301, filed on Apr. 3, 2017, entitled, "Color Analysis And Control Using An Electronic Mobile Device Transparent Display Screen," now U.S. Pat. No. 10,116,924, issued May 10, 2018, which is a Continuation-in-part of U.S. patent application Ser. No. 15/477,131, filed on Apr. 3, 2017, entitled, "Method And System For Correlating Anatomy Using An Electronic Mobile Device Transparent Display Screen," now U.S. Pat. No. 9,801,693, issued Oct. 31, 2017, which is a Continuation-in-part of U.S. patent application Ser. No. 15/464,231, filed on Mar. 20, 2017, now abandoned, which is a Continuation-in-part of U.S. provisional patent application Ser. No. 62/420,544, filed on Nov. 10, 2016.

FIELD OF THE INVENTION

The present disclosure relates to methods and systems using transparent display screens in mobile electronic devices and, more particularly to a method and system for method and system for correlating anatomy using an electronic mobile device transparent display screen. Even more particularly, the present disclosure relates to a method, system, and integrated medical imaging system for forming a correlated view of human or other animal anatomy with electromagnetic spectrum images with non-optical electromagnetic images of human or other animal anatomy.

BACKGROUND OF THE INVENTION

Electronic mobile devices are improving display screens and technical capabilities. With SoC (system on chip) making hardware in nanometer critical dimension size and being reduced smaller. Hardware miniaturized to be concealed behind small areas making it possible to incorporate transparent screens for electronic mobile device. However, with transparent screen, privacy can be an issue. As these mobile devices have become popular, there is a need for more functions in transparent display screens.

Displaying images on an electronic device and, in some embodiments, on a transparent electronic device gives rise to numerous advantages that are just beginning to be conceived and realized. In certain embodiments, the transparent portion may encompass the entire viewing area, or only a portion of the viewing area of a device.

The present disclosure generally relates to an electronic device that includes a display screen having a viewing area with a transparent portion enabling a user to view objects behind the electronic device by looking at the display screen for forming a correlated view of human or other animal anatomy with electromagnetic spectrum images with non-optical electromagnetic images of human or other animal anatomy. The electronic device may further include one or more electronic components, including a power source, processor, and circuitry for transmitting signals representative of image data to the display. In certain embodiments, the transparent portion may encompass the entire viewing area, or only a portion of the viewing area of the display.

Furthermore, in additional embodiments, the electronic device may include two or more of such display screens whereby one display screen includes an opaque region, but also provides a movable transparent window. In another embodiment, the device may include one or more active and/or one or more passive display screens that may be utilized based on the resolution of an image to be displayed as well as the sensed rotation of the device.

In additional embodiments, the electronic device may include two or more of such display screens (each having respective viewing areas with transparent portions) arranged in an overlaid or back-to-back manner. Furthermore, in additional embodiments, the electronic device may include two or more of such display screens whereby one display screen is partially opaque, but displays a movable transparent window thereon. The moveable window may, in one embodiment, be moved based on user input in the form of touching of a touch screen.

In another embodiment, the device may include one or more active and/or one or more passive display screens. These screens may be utilized based on a comparison of the resolution of an image to be displayed with a threshold level. Furthermore, the utilization of the display screens may be based on sensed rotation of the device.

BRIEF SUMMARY OF THE INVENTION

The disclosed subject matter provides a method, system, and integrated medical imaging system for forming a correlated view of human or other animal anatomy with electromagnetic spectrum images with non-optical electromagnetic images of human or other animal anatomy.

In summary, the present disclosure provides a method, system, and integrated medical imaging system for forming a correlated view of human or other animal anatomy using at least one transparent display screen associated with an electronic mobile device. The view relates an optical view with other electromagnetic spectrum images with a non-optical electromagnetic image of selected portions of human or other animal anatomy. The disclosure associates at least three visible position markers with selected positions of a predetermined portion of human or other animal anatomy. The at least three visible position markers provide a predetermined measure of opacity for selected non-optical electromagnetic frequencies. The method and system imaging the predetermined portion of human or other animal anatomy using at least a subset of selected non-optical electromagnetic frequencies using an electromagnetic imaging device optical electromagnetic image of said predetermined portion of human or other animal anatomy. The at least three visible position markers and at least three visible position markers exhibit at least partial opacity for at least one of said subset of selected non-optical electromagnetic frequencies. The method and system forming an optical view of the predetermined portion of human or other animal anatomy through at least a portion of a transparent display screen associated with said electronic mobile device. The disclosure forms a correlated view of the predetermined portion of human or other animal anatomy by relating said at least one non-optical electromagnetic image of the at least three visible position markers with a visual image of said at least three visible position markers. The view correlates the size and dimensions of the optical view and non-optical electromagnetic image of the predetermined portion of human or other animal anatomy.

An important aspect of the present disclosure includes incorporating a 3D camera and/or optical sensor with RF, Bluetooth, and/or NFC sensors and with use of software and algorithms to existing medical imaging devices such as CT scanner, MRI, hand held cardiovascular scanner with Doppler technology. This configuration will scan and record distinct points prior or during imaging. These points may be used as benchmark locations for use of Law of Cosine to align and incorporate images from different device to be displayed together or at user's preference for viewing which contents displayed on a mobile device. Such a mobile device may include a transparent display screen or conventional LED, OLED non-transparent screen with can be shown in AR/MR image on a mobile device screen.

Using software and 3D sensor's recorded position information (benchmark location), a minimum of three or more points (Law of Cosine) can be used to locate the updated position of the superimposed radiograph or MRI image on to the actual anatomy. Multiple RDF and/or Bluetooth markers may work in conjunction with 3D sensors for improved accuracy. With collection of all data, application to refine augmented reality (AR), mixed reality (MR), or AR translucent parallax image superimposed on to actual part of anatomy.

Benefits of the presently disclosed subject matter include improved accuracy, enhanced translucent parallax images, and the ability to track AR image size (Law of Cosine). Moreover, the present disclosure provides the ability to adjust depth and angle of AR image, adjust angle of parallax images, and align users display viewing angle.

According to certain aspects, there is here provided a method and system for utilization of a transparent display screens on mobile electronic device with multiple transparent display screens layered, bonded or formed monolithic. The disclosure includes utilization of transparent display screen for study of human anatomy with incorporating X-ray radiography, magnetic resonance imaging, etc., to display onto transparent display screen. Images taken with imaging device are overlayed onto the portion of subject that has been imaged. For multiple transparent display layered screen, the same area of image is used, but images of different level of imaging such as tissue, organ, and skeletal image is to be shown on different layer of transparent display layers in parallax image. For accuracy for displaying imaged/scanned area on transparent display layer, by placing at least 3 non-translucent/radio-opaque X-ray markers for identification of X, Y & Z (Law of Cosine) to keep coordinates utilizing on board camera on mobile device for tracking.

According to another aspect of the present disclosure, there is here provided the ability to align the sensors so that if there are multiple surgeries there is the ability to employ a parallax image and the ability to go deeper into images with the use of hand gestures that vary with intensity and duration. The present disclosure provides the ability to align sensors and perceptions through a transparent display screen of a mobile electronic device with x-ray image with the optical image appearing on the display.

In yet another aspect of the present disclosure there is provided an electronic mobile device with multiple layered transparent display screens. The method and system use the display of transparent screens on mobile device for study of anatomy. Electronic mobile device with transparent screens will include electronic components, which makes the device function. Enhancement of transparent display screens by, utilizing layers of transparent display screen to show different layers of images per display layer.

One of the aspects of the present disclosure includes the ability to control perceptions of texture and depth using varying amounts of pressure applied to screen the transparent screen. That's come up for a sample, the ability to control the perceived depth of a particular object by virtue of pressing harder or softer on the screen or doing so with greater or less or speed.

And alternative embodiment of the present disclosure incorporates the concept of having dual trans parent screens. These dual transparent screens have the ability to determine wearing aspects of parallax images. As more sophistication arises in the use of transparent screens and multiple transparent screens, the ability to control the perceive the way images are collected and maybe responded to using multiple screens.

BRIEF DESCRIPTION OF THE DRAWINGS

The present subject matter will now be described in detail with reference to the drawings, which are provided as illustrative examples of the subject matter so as to enable those skilled in the art to practice the subject matter. Notably, the FIGUREs and examples are not meant to limit the scope of the present subject matter to a single embodiment, but other embodiments are possible by way of interchange of some or all of the described or illustrated elements and, further, wherein.

DETAILED DESCRIPTION OF ILLUSTRATIVE EMBODIMENTS

Figure 1:
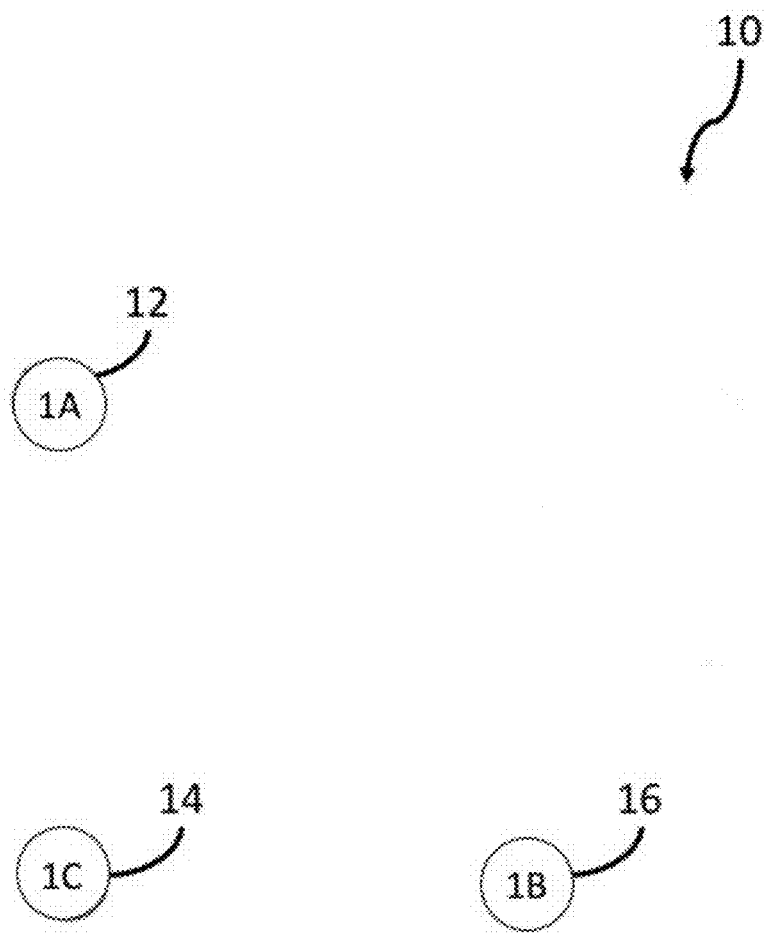
FIG. 1 is view of radio-opaque markers/tags. Which can be imbedded with sensors or reattach able feed sensors for viewing coordinate accuracy.

The detailed description set forth below in connection with the appended drawings is intended as a description of exemplary embodiments in which the presently disclosed process can be practiced. The term "exemplary" used throughout this description means "serving as an example, instance, or illustration," and should not necessarily be construed as preferred or advantageous over other embodiments. The detailed description includes specific details for providing a thorough understanding of the presently disclosed method and system. However, it will be apparent to those skilled in the art that the presently disclosed process may be practiced without these specific details. In some instances, well-known structures and devices are shown in block diagram form in order to avoid obscuring the concepts of the presently disclosed method and system.

In the present specification, an embodiment showing a singular component should not be considered limiting. Rather, the subject matter preferably encompasses other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present subject matter encompasses present and future known equivalents to the known components referred to herein by way of illustration.

Transparent display screen for mobile device usage for anatomy study. The present disclosure provides a method and system for utilization of a transparent display screens on mobile electronic device with multiple transparent display screens layered, bonded or formed monolithic. Utilization of transparent display screen for study of human anatomy with incorporating X-ray radiography, magnetic resonance imaging, etc., to display onto transparent display screen. Images taken with imaging device is overlay onto the portion of subject that has been imaged. For multiple transparent display layered screen, same area of image but images of different level of imaging such as tissue, organ, and skeletal image is to be shown on different layer of transparent display layers in parallax image. For accuracy for displaying imaged/scanned area on transparent display layer, by placing at least 3 non-translucent/radio-opaque X-ray markers for identification of X, Y & Z (Law of Cosine) to keep coordinates utilizing on board camera on mobile device for tracking.

Prior to X-ray radiography, magnetic resonance imaging, etc., image is taken, utilizing onboard camera to take reference photo of coordinates of radio-opaque markers from same distance. After the images are taken by imaging technologies like X-ray radiography, magnetic resonance imaging, etc., image is overlay on to transparent display layer while viewing over subject area though the transparent display, and camera software utilizes previous reference photo with at least 3 tracking coordinates to keep accuracy. For further accuracy, RF, Bluetooth, type of sensors (sensors which will function after radiograph) may be imbedded on to radio opaque markers or reattached over the markers adhesive onto the subject area, which mobile device receives feedbacks to keep X-Ray radiograph image coordination with areas viewed though transparent display screen.

After imaging technologies like X-ray radiography, magnetic resonance imaging, etc. has been taken, using mobile device with transparent display to view imaged area while radiograph image is overlayed on to subject area as viewed though transparent display screen.

For accuracy of viewing subject area imaged with imaging technologies like X-ray radiography, magnetic resonance imaging, etc., utilizing attached radio-opaque tags, and or radio-opaque tags with electronic sensors imbedded or reattach able after radiograph imaged, and or camera base app to keep track of areas imaged as viewed though transparent display screen.

For multiple transparent display layered screen, multiple layers of anatomy images taken by imaging technologies like X-ray radiography, magnetic resonance imaging, etc., show anatomy layers per transparent display layer in parallax image for enhanced visual effect, while device user has option to turn off selected layer of anatomy or may view at same time overlay on to subject area.

Electronic mobile device are improving display screens and technical capabilities. With SoC (system on chip) making hardware in Nano size and being reduced smaller. Hardware miniaturized to be concealed behind small areas making it possible to incorporate transparent screens for electronic mobile device. However with transparent screen, privacy can be an issue. As these mobile devices have become popular, there is a need for more functions in transparent display screens.

FIG. 1 is view of radio-opaque markers/tags 10, 12, and 14. Which can be imbedded with sensors or reattach able feed sensors for viewing coordinate accuracy.

Figure 2:
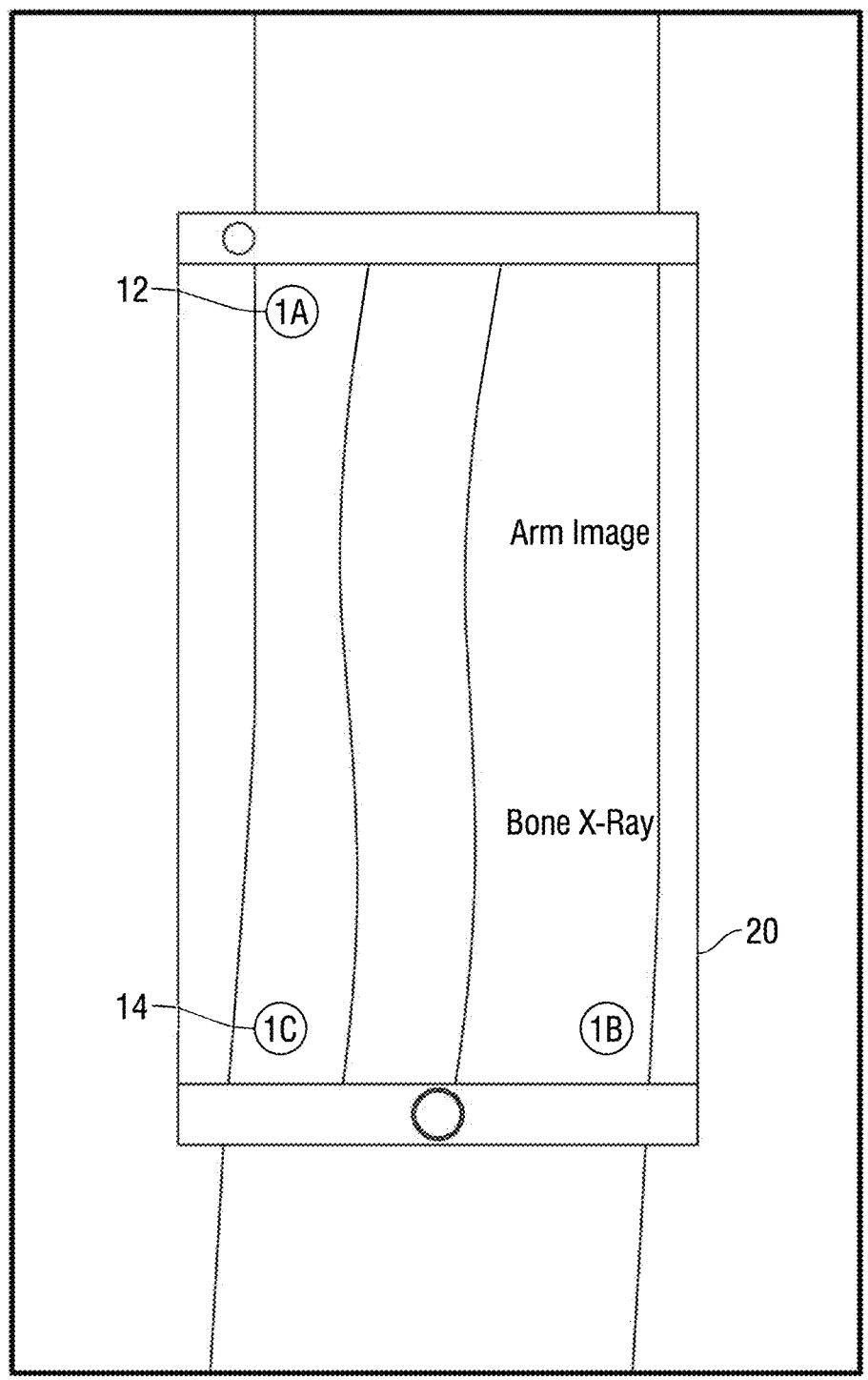
FIG. 2 is view of radiograph image displayed though transparent display screen while viewing over radiographed area.

FIG. 2 is view of radiograph image 16 displayed though transparent display screen 18 while viewing over radiographed area 16. Radio-opaque markers 10, 12, and 14 are shown though the transparent display screen 18.

Figure 3:
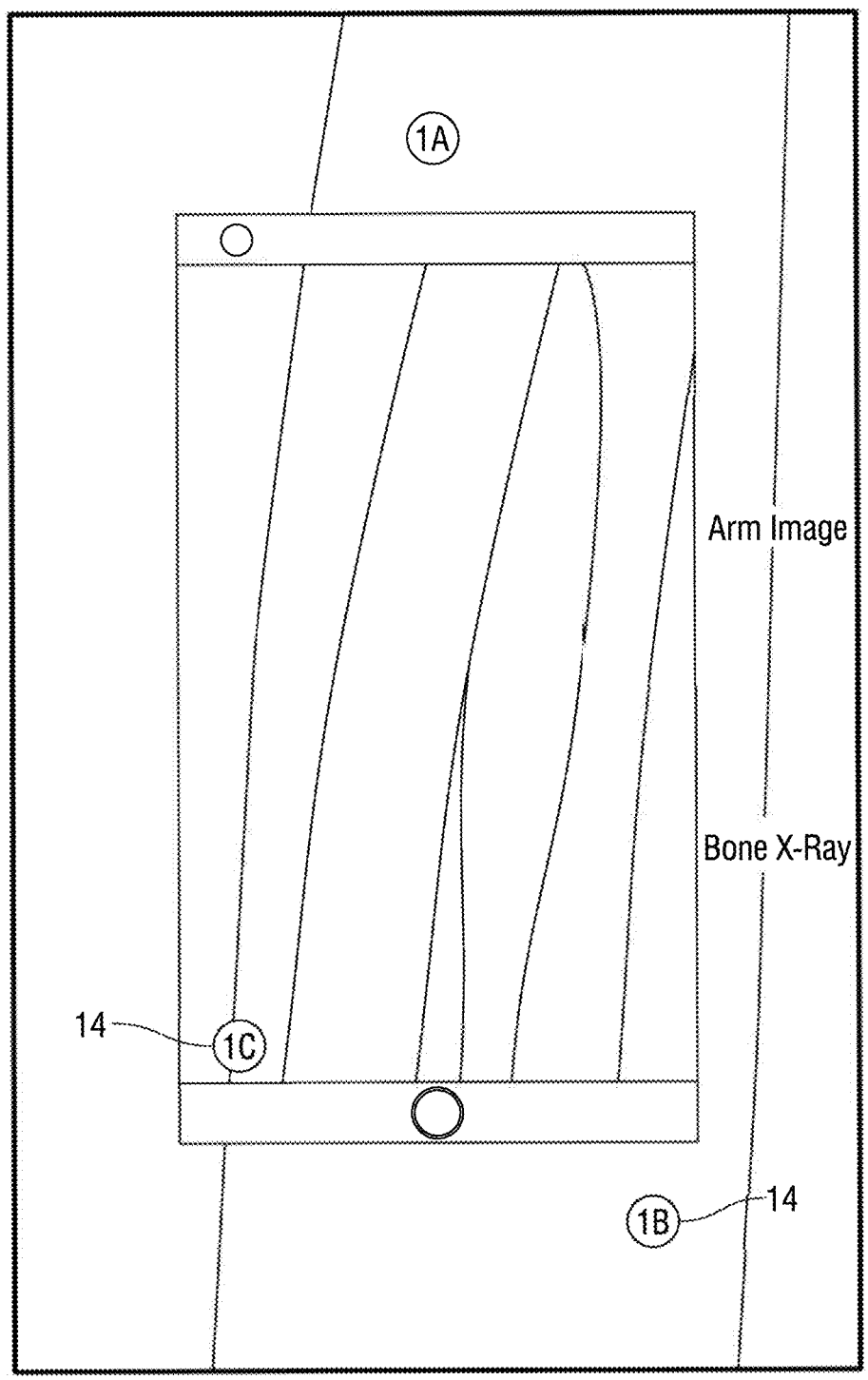
FIG. 3 is view of radiograph image displayed though transparent display screen while viewing over radiographed area. Radio-opaque markers with sensor are shown though the transparent display screen and outside the transparent display screen area.

FIG. 3 is view of radiograph image 16 displayed though transparent display screen 18 while viewing over radiographed area 16. Radio-opaque markers 10, 12, and 14 with sensor are shown though the transparent display screen and outside the transparent display screen area.

The disclosed subject matter provides a method, system, and integrated imaging platform for forming a correlated view of human or other animal anatomy using at least one transparent display screen associated with an electronic mobile device, the view relating an optical view with other electromagnetic spectrum images with a non-optical electromagnetic image of selected portions of human or other animal anatomy, the method comprising the steps of: associating at least three visible position markers with selected positions of a predetermined portion of human or other animal anatomy, the at least three visible position markers comprising a predetermined measure of opacity for selected non-optical electromagnetic frequencies.

The process images the predetermined portion of human or other animal anatomy using at least a subset of the selected non-optical electromagnetic frequencies using an electromagnetic imaging device for forming at least one non-optical electromagnetic image of the predetermined portion of human or other animal anatomy, including the at least three visible position markers and further wherein the at least three visible position markers exhibit at least partial opacity for at least one of the subset of selected non-optical electromagnetic frequencies.

The process further forms an optical view of the predetermined portion of human or other animal anatomy through at least a portion of a transparent display screen associated with the electronic mobile device. Then, the process forms a correlated view of the predetermined portion of human or other animal anatomy by relating the at least one non-optical electromagnetic image of the at least three visible position markers with a visual image of the at least three visible position markers, the correlated view correlating the size and dimensions of the optical view and the at least one non-optical electromagnetic image of the predetermined portion of human or other animal anatomy.

For the disclosed method and system, the non-optical electromagnetic frequencies comprise X-ray frequencies and the at least one non-optical electromagnetic image may be an X-ray image. The non-optical electromagnetic frequencies comprise magnetic resonance frequencies and the at least one non-optical electromagnetic image may be a magnetic resonance image. The predetermined portion of human or other animal anatomy comprises flesh tissue. The predetermined portion of human or other animal anatomy may be skeletal anatomy.

The at least three visible position markers exhibit at least partial opacity to a plurality of non-optical electromagnetic frequencies. The at least three visible position markers further comprise electromagnetic transmitters for transmitting position signals from the selected positions of the predetermined portion of the human or other animal anatomy. The at least three visible position markers further comprise RF transmitters for transmitting position signals from the selected positions of the predetermined portion of the human or other animal anatomy.

The at least three visible position markers further comprise Bluetooth transmitters for transmitting position signals from the selected positions of the predetermined portion of the human or other animal anatomy. The system of claim 8, further comprising the step displaying the correlated view of the predetermined portion of human or other animal anatomy as a parallax image for enhancing visual effects associating with the correlated view.

U.S. Pat. No. 9,367,093 to Pance, issued on Jun. 14, 2016 describes and claims a "Transparent Electronic Device for displaying images on a transparent display of an electronic device. The display may include one or more display screens as well as a flexible circuit for connecting the display screens with internal circuitry of the electronic device. Furthermore, the display screens may allow for overlaying of images over real world viewable objects, as well as a visible window to be present on an otherwise opaque display screen. Additionally, the display may include active and passive display screens that may be utilized based on images to be displayed. The disclosure of U.S. Pat. No. 9,367,093 is expressly incorporated by reference, as though contained fully herein.

Figure 4A:
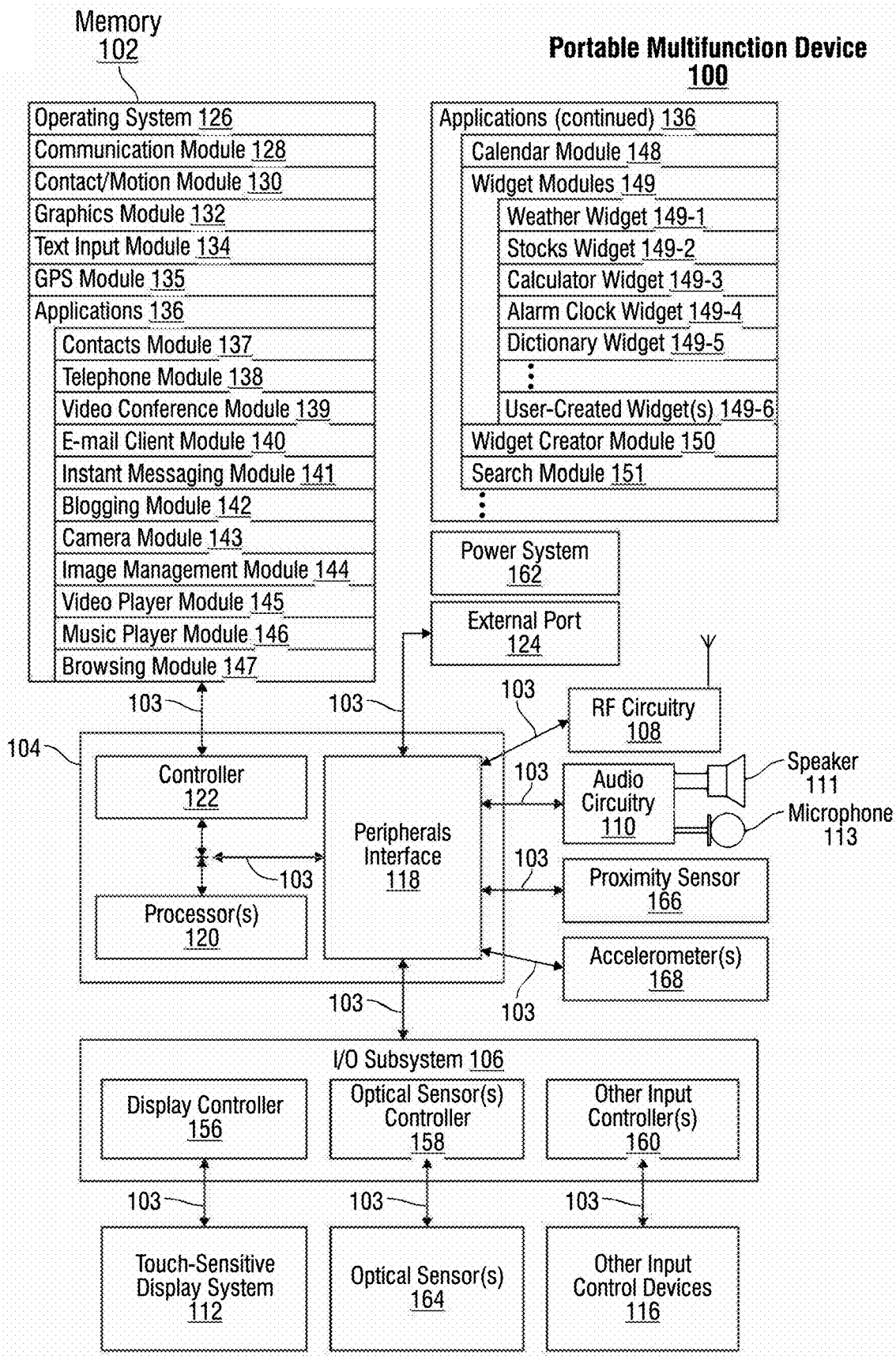
FIGS. 4A and 4B are block diagrams illustrating portable multifunction devices with touch-sensitive displays in accordance with some embodiments.
Figure 4B:
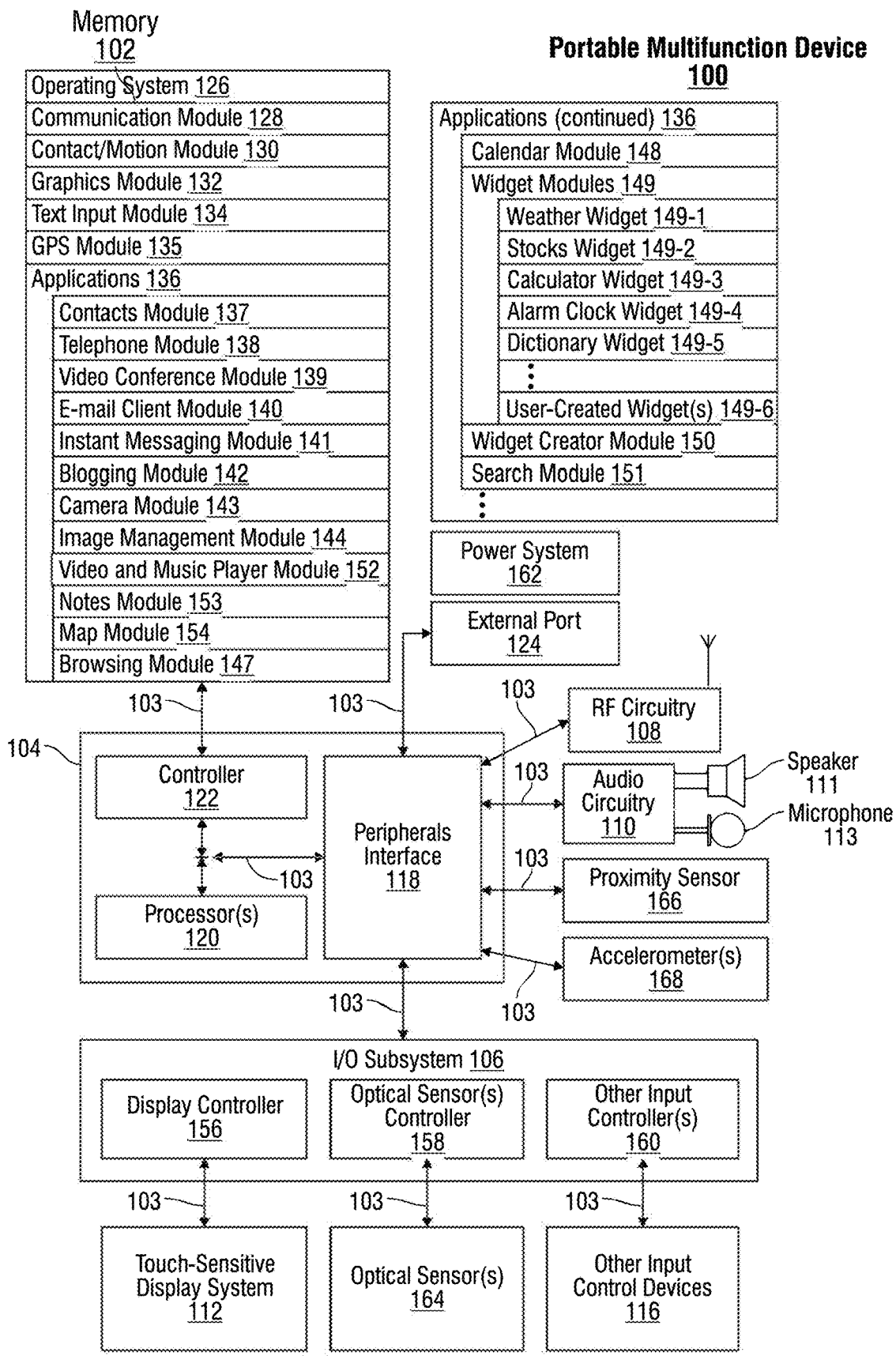

FIGS. 4A and 4B are block diagrams illustrating portable multifunction devices 100 with touch-sensitive displays 112 in accordance with some embodiments for the presently disclosed method, system, and integrated medical imaging system for forming a correlated view of human or other animal anatomy with electromagnetic spectrum images with non-optical electromagnetic images of human or other animal anatomy. The touch-sensitive display 112 is sometimes called a "touch screen" for convenience, and may also be known as or called a touch-sensitive display system. The device 100 may include a memory 102 (which may include one or more computer readable storage mediums), a memory controller 122, one or more processing units (CPU's) 120, a peripherals interface 118, RF circuitry 108, audio circuitry 110, a speaker 111, a microphone 113, an input/output (I/O) subsystem 106, other input or control devices 116, and an external port 124. The device 100 may include one or more optical sensors 164. These components may communicate over one or more communication buses or signal lines 103.

It should be appreciated that the device 100 is only one example of a portable multifunction device 100, and that the device 100 may have more or fewer components than shown, may combine two or more components, or a may have a different configuration or arrangement of the components. The various components shown in FIGS. 1A and 1B may be implemented in hardware, software or a combination of both hardware and software, including one or more signal processing and/or application specific integrated circuits.

Memory 102 may include high-speed random access memory and may also include non-volatile memory, such as one or more magnetic disk storage devices, flash memory devices, or other non-volatile solid-state memory devices. Access to memory 102 by other components of the device 100, such as the CPU 120 and the peripherals interface 118, may be controlled by the memory controller 122.

The peripherals interface 118 couples the input and output peripherals of the device to the CPU 120 and memory 102. The one or more processors 120 run or execute various software programs and/or sets of instructions stored in memory 102 to perform various functions for the device 100 and to process data.

In some embodiments, the peripherals interface 118, the CPU 120, and the memory controller 122 may be implemented on a single chip, such as a chip 104. In some other embodiments, they may be implemented on separate chips.

The RF (radio frequency) circuitry 108 receives and sends RF signals, also called electromagnetic signals. The RF circuitry 108 converts electrical signals to/from electromagnetic signals and communicates with communications networks and other communications devices via the electromagnetic signals. The RF circuitry 108 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth.

The RF circuitry 108 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

The audio circuitry 110, the speaker 111, and the microphone 113 provide an audio interface between a user and the device 100. The audio circuitry 110 receives audio data from the peripherals interface 118, converts the audio data to an electrical signal, and transmits the electrical signal to the speaker 111. The speaker 111 converts the electrical signal to human-audible sound waves. The audio circuitry 110 also receives electrical signals converted by the microphone 113 from sound waves. The audio circuitry 110 converts the electrical signal to audio data and transmits the audio data to the peripherals interface 118 for processing. Audio data may be retrieved from and/or transmitted to memory 102 and/or the RF circuitry 108 by the peripherals interface 118. In some embodiments, the audio circuitry 110 also includes a headset jack (e.g. 212, FIG. 2). The headset jack provides an interface between the audio circuitry 110 and removable audio input/output peripherals, such as output-only headphones or a headset with both output (e.g., a headphone for one or both ears) and input (e.g., a microphone).

The I/O subsystem 106 couples input/output peripherals on the device 100, such as the touch screen 112 and other input/control devices 116, to the peripherals interface 118. The I/O subsystem 106 may include a display controller 156 and one or more input controllers 160 for other input or control devices. The one or more input controllers 160 receive/send electrical signals from/to other input or control devices 116. The other input/control devices 116 may include physical buttons (e.g., push buttons, rocker buttons, etc.), dials, slider switches, joysticks, click wheels, and so forth. In some alternate embodiments, input controller(s) 160 may be coupled to any (or none) of the following: a keyboard, infrared port, USB port, and a pointer device such as a mouse. The one or more buttons (e.g., 208, FIG. 5) may include an up/down button for volume control of the speaker 111 and/or the microphone 113. The one or more buttons may include a push button (e.g., 206, FIG. 2). A quick press of the push button may disengage a lock of the touch screen 112 or begin a process that uses gestures on the touch screen to unlock the device, as described in U.S. patent application Ser. No. 11/322,549, "Unlocking a Device by Performing Gestures on an Unlock Image," filed Dec. 23, 2005, which is hereby incorporated by reference in its entirety. A longer press of the push button (e.g., 206) may turn power to the device 100 on or off. The user may be able to customize a functionality of one or more of the buttons. The touch screen 112 is used to implement virtual or soft buttons and one or more soft keyboards.

The touch-sensitive touch screen 112 provides an input interface and an output interface between the device and a user. The display controller 156 receives and/or sends electrical signals from/to the touch screen 112. The touch screen 112 displays visual output to the user. The visual output may include graphics, text, icons, video, and any combination thereof (collectively termed "graphics"). In some embodiments, some or all of the visual output may correspond to user-interface objects, further details of which are described below.

A touch screen 112 has a touch-sensitive surface, sensor or set of sensors that accepts input from the user based on haptic and/or tactile contact. The touch screen 112 and the display controller 156 (along with any associated modules and/or sets of instructions in memory 102) detect contact (and any movement or breaking of the contact) on the touch screen 112 and converts the detected contact into interaction with user-interface objects (e.g., one or more soft keys, icons, web pages or images) that are displayed on the touch screen. In an exemplary embodiment, a point of contact between a touch screen 112 and the user corresponds to a finger of the user.

The touch screen 112 may use LCD (liquid crystal display) technology, or LPD (light emitting polymer display) technology, although other display technologies may be used in other embodiments. The touch screen 112 and the display controller 156 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 112.

A touch-sensitive display in some embodiments of the touch screen 112 may be analogous to the multi-touch sensitive tablets described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in their entirety. However, a touch screen 112 displays visual output from the portable device 100, whereas touch sensitive tablets do not provide visual output.

A touch-sensitive display in some embodiments of the touch screen 112 may be as described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

The touch screen 112 may have a resolution in excess of 100 dpi. In an exemplary embodiment, the touch screen has a resolution of approximately 160 dpi. The user may make contact with the touch screen 112 using any suitable object or appendage, such as a stylus, a finger, and so forth. In some embodiments, the user interface is designed to work primarily with finger-based contacts and gestures, which are much less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, the device 100 may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from the touch screen 112 or an extension of the touch-sensitive surface formed by the touch screen.

The device 100 also includes a power system 162 for powering the various components. The power system 162 may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

The device 100 may also include one or more optical sensors 164. FIGS. 4A and 4B show an optical sensor coupled to an optical sensor controller 158 in I/O subsystem 106. The optical sensor 164 may include charge-coupled device (CCD) or complementary metal-oxide semiconductor (CMOS) phototransistors. The optical sensor 164 receives light from the environment, projected through one or more lens, and converts the light to data representing an image. In conjunction with an imaging module 143 (also called a camera module), the optical sensor 164 may capture still images or video. In some embodiments, an optical sensor is located on the back of the device 100, opposite the touch screen display 112 on the front of the device, so that the touch screen display may be used as a viewfinder for either still and/or video image acquisition.

In some embodiments, an optical sensor is located on the front of the device so that the user's image may be obtained for videoconferencing while the user views the other video conference participants on the touch screen display. In some embodiments, the position of the optical sensor 164 can be changed by the user (e.g., by rotating the lens and the sensor in the device housing) so that a single optical sensor 164 may be used along with the touch screen display for both video conferencing and still and/or video image acquisition.

The device 100 may also include one or more proximity sensors 166. FIGS. 4A and 4B show a proximity sensor 166 coupled to the peripherals interface 118. Alternately, the proximity sensor 166 may be coupled to an input controller 160 in the I/O subsystem 106. The proximity sensor 166 may perform as described in U.S. patent application Ser. No. 11/241,839, "Proximity Detector In Handheld Device," filed Sep. 30, 2005; Ser. No. 11/240,788, "Proximity Detector In Handheld Device," filed Sep. 30, 2005; Ser. No. 11/620,702, "Using Ambient Light Sensor To Augment Proximity Sensor Output"; Ser. No. 11/586,862, "Automated Response To And Sensing Of User Activity In Portable Devices," filed Oct. 24, 2006; and Ser. No. 11/638,251, "Methods And Systems For Automatic Configuration Of Peripherals," which are hereby incorporated by reference in their entirety. In some embodiments, the proximity sensor turns off and disables the touch screen 112 when the multifunction device is placed near the user's ear (e.g., when the user is making a phone call). In some embodiments, the proximity sensor keeps the screen off when the device is in the user's pocket, purse, or other dark area to prevent unnecessary battery drainage when the device is a locked state.

The device 100 may also include one or more accelerometers 168. FIGS. 4A and 4B show an accelerometer 168 coupled to the peripherals interface 118. Alternately, the accelerometer 168 may be coupled to an input controller 160 in the I/O subsystem 106. The accelerometer 168 may perform as described in U.S. Patent Publication No. 20050190059, "Acceleration-based Theft Detection System for Portable Electronic Devices," and U.S. Patent Publication No. 20060017692, "Methods and Apparatuses For Operating A Portable Device Based On An Accelerometer," both of which are which are incorporated by reference in their entirety. In some embodiments, information is displayed on the touch screen display in a portrait view or a landscape view based on an analysis of data received from the one or more accelerometers.

In some embodiments, the software components stored in memory 102 may include an operating system 126, a communication module (or set of instructions) 128, a contact/motion module (or set of instructions) 130, a graphics module (or set of instructions) 132, a text input module (or set of instructions) 134, a Global Positioning System (GPS) module (or set of instructions) 135, and applications (or set of instructions) 136.

The operating system 126 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

The communication module 128 facilitates communication with other devices over one or more external ports 124 and also includes various software components for handling data received by the RF circuitry 108 and/or the external port 124. The external port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with the 30-pin connector used on iPod (trademark of Apple Computer, Inc.) devices.

The contact/motion module 130 may detect contact with the touch screen 112 (in conjunction with the display controller 156) and other touch sensitive devices (e.g., a touchpad or physical click wheel). The contact/motion module 130 includes various software components for performing various operations related to detection of contact, such as determining if contact has occurred, determining if there is movement of the contact and tracking the movement across the touch screen 112, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/multiple finger contacts). In some embodiments, the contact/motion module 130 and the display controller 156 also detects contact on a touchpad. In some embodiments, the contact/motion module 130 and the controller 160 detects contact on a click wheel.

The graphics module 132 includes various known software components for rendering and displaying graphics on the touch screen 112, including components for changing the intensity of graphics that are displayed. As used herein, the term "graphics" includes any object that can be displayed to a user, including without limitation text, web pages, icons (such as user-interface objects including soft keys), digital images, videos, animations and the like. An animation in this context is a display of a sequence of images that gives the appearance of movement, and informs the user of an action that has been performed (such as moving an email message to a folder). In this context, a respective animation that confirms an action by the user of the device typically takes a predefined, finite amount of time, such as an amount of time between 0.2 and 1.0 seconds, or between 0.5 and 2.0 seconds, depending on the context.

The text input module 134, which may be a component of graphics module 132, provides soft keyboards for entering text in various applications (e.g., contacts 137, e-mail 140, IM 141, blogging 142, browser 147, and any other application that needs text input).

The GPS module 135 determines the location of the device and provides this information for use in various applications (e.g., to telephone 138 for use in location-based dialing, to camera 143 and/or blogger 142 as picture/video metadata, and to applications that provide location-based services such as weather widgets, local yellow page widgets, and map/navigation widgets).

The applications 136 may include the following modules (or sets of instructions), or a subset or superset thereof:

- a contacts module 137 (sometimes called an address book or contact list);
- a telephone module 138;
- a video conferencing module 139;
- an e-mail client module 140;
- an instant messaging (IM) module 141;
- a blogging module 142;
- a camera module 143 for still and/or video images;
- an image management module 144;
- a video player module 145;
- a music player module 146;
- a browser module 147;
- a calendar module 148;
- widget modules 149, which may include weather widget 149-1, stocks widget 149-2, calculator widget 149-3, alarm clock widget 149-4, dictionary widget 149-5, and other widgets obtained by the user, as well as user-created widgets 149-6;
- widget creator module 150 for making user-created widgets 149-6;
- search module 151;
- video and music player module 152, which merges video player module 145 and music player module 146;
- notes module 153; and/or
- map module 154.

Examples of other applications 136 that may be stored in memory 102 include other word processing applications, JAVA-enabled applications, encryption, digital rights management, voice recognition, and voice replication.

In conjunction with touch screen 112, display controller 156, contact module 130, graphics module 132, and text input module 134, the contacts module 137 may be used to manage an address book or contact list, including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference 139, e-mail 140, or IM 141; and so forth. Embodiments of user interfaces and associated processes using contacts module 137 are described further below.

In conjunction with RF circuitry 108, audio circuitry 110, speaker 111, microphone 113, touch screen 112, display controller 156, contact module 130, graphics module 132, and text input module 134, the telephone module 138 may be used to enter a sequence of characters corresponding to a telephone number, access one or more telephone numbers in the address book 137, modify a telephone number that has been entered, dial a respective telephone number, conduct a conversation and disconnect or hang up when the conversation is completed. As noted above, the wireless communication may use any of a plurality of communications standards, protocols and technologies. Embodiments of user interfaces and associated processes using telephone module 138 are described further below.

In conjunction with RF circuitry 108, audio circuitry 110, speaker 111, microphone 113, touch screen 112, display controller 156, optical sensor 164, optical sensor controller 158, contact module 130, graphics module 132, text input module 134, contact list 137, and telephone module 138, the videoconferencing module 139 may be used to initiate, conduct, and terminate a video conference between a user and one or more other participants.

In conjunction with RF circuitry 108, touch screen 112, display controller 156, contact module 130, graphics module 132, and text input module 134, the e-mail client module 140 may be used to create, send, receive, and manage e-mail. In conjunction with image management module 144, the e-mail module 140 makes it very easy to create and send e-mails with still or video images taken with camera module 143. Embodiments of user interfaces and associated processes using e-mail module 140 are described further below.

In conjunction with RF circuitry 108, touch screen 112, display controller 156, contact module 130, graphics module 132, and text input module 134, the instant messaging module 141 may be used to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages and to view received instant messages. In some embodiments, transmitted and/or received instant messages may include graphics, photos, audio files, video files and/or other attachments as are supported in a MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS). Embodiments of user interfaces and associated processes using instant messaging module 141 are described further below.

In conjunction with RF circuitry 108, touch screen 112, display controller 156, contact module 130, graphics module 132, text input module 134, image management module 144, and browsing module 147, the blogging module 142 may be used to send text, still images, video, and/or other graphics to a blog (e.g., the user's blog).

In conjunction with touch screen 112, display controller 156, optical sensor(s) 164, optical sensor controller 158, contact module 130, graphics module 132, and image management module 144, the camera module 143 may be used to capture still images or video (including a video stream) and store them into memory 102, modify characteristics of a still image or video, or delete a still image or video from memory 102. Embodiments of user interfaces and associated processes using camera module 143 are described further below.

In conjunction with touch screen 112, display controller 156, contact module 130, graphics module 132, text input module 134, and camera module 143, the image management module 144 may be used to arrange, modify or otherwise manipulate, label, delete, present (e.g., in a digital slide show or album), and store still and/or video images. Embodiments of user interfaces and associated processes using image management module 144 are described further below.

In conjunction with touch screen 112, display controller 156, contact module 130, graphics module 132, audio circuitry 110, and speaker 111, the video player module 145 may be used to display, present or otherwise play back videos (e.g., on the touch screen or on an external, connected display via external port 124). Embodiments of user interfaces and associated processes using video player module 145 are described further below.

In conjunction with touch screen 112, display system controller 156, contact module 130, graphics module 132, audio circuitry 110, speaker 111, RF circuitry 108, and browser module 147, the music player module 146 allows the user to download and play back recorded music and other sound files stored in one or more file formats, such as MP3 or AAC files. In some embodiments, the device 100 may include the functionality of an MP3 player, such as an iPod (trademark of Apple Computer, Inc.). Embodiments of user interfaces and associated processes using music player module 146 are described further below.

In conjunction with RF circuitry 108, touch screen 112, display system controller 156, contact module 130, graphics module 132, and text input module 134, the browser module 147 may be used to browse the Internet, including searching, linking to, receiving, and displaying web pages or portions thereof, as well as attachments and other files linked to web pages. Embodiments of user interfaces and associated processes using browser module 147 are described further below.

In conjunction with RF circuitry 108, touch screen 112, display system controller 156, contact module 130, graphics module 132, text input module 134, e-mail module 140, and browser module 147, the calendar module 148 may be used to create, display, modify, and store calendars and data associated with calendars (e.g., calendar entries, to do lists, etc.). Embodiments of user interfaces and associated processes using calendar module 148 are described further below.

In conjunction with RF circuitry 108, touch screen 112, display system controller 156, contact module 130, graphics module 132, text input module 134, and browser module 147, the widget modules 149 are mini-applications that may be downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display system controller 156, contact module 130, graphics module 132, text input module 134, and browser module 147, the widget creator module 150 may be used by a user to create widgets (e.g., turning a user-specified portion of a web page into a widget).

In conjunction with touch screen 112, display system controller 156, contact module 130, graphics module 132, and text input module 134, the search module 151 may be used to search for text, music, sound, image, video, and/or other files in memory 102 that match one or more search criteria (e.g., one or more user-specified search terms).

In conjunction with touch screen 112, display controller 156, contact module 130, graphics module 132, and text input module 134, the notes module 153 may be used to create and manage notes, to do lists, and the like.

In conjunction with RF circuitry 108, touch screen 112, display system controller 156, contact module 130, graphics module 132, text input module 134, GPS module 135, and browser module 147, the map module 154 may be used to receive, display, modify, and store maps and data associated with maps (e.g., driving directions; data on stores and other points of interest at or near a particular location; and other location-based data).

Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments. For example, video player module 145 may be combined with music player module 146 into a single module (e.g., video and music player module 152, FIG. 4B). In some embodiments, memory 102 may store a subset of the modules and data structures identified above. Furthermore, memory 102 may store additional modules and data structures not described above.

In some embodiments, the device 100 is a device where operation of a predefined set of functions on the device is performed exclusively through a touch screen 112 and/or a touchpad. By using a touch screen and/or a touchpad as the primary input/control device for operation of the device 100, the number of physical input/control devices (such as push buttons, dials, and the like) on the device 100 may be reduced.

The predefined set of functions that may be performed exclusively through a touch screen and/or a touchpad include navigation between user interfaces. In some embodiments, the touchpad, when touched by the user, navigates the device 100 to a main, home, or root menu from any user interface that may be displayed on the device 100. In such embodiments, the touchpad may be referred to as a "menu button." In some other embodiments, the menu button may be a physical push button or other physical input/control device instead of a touchpad.

Figure 5:
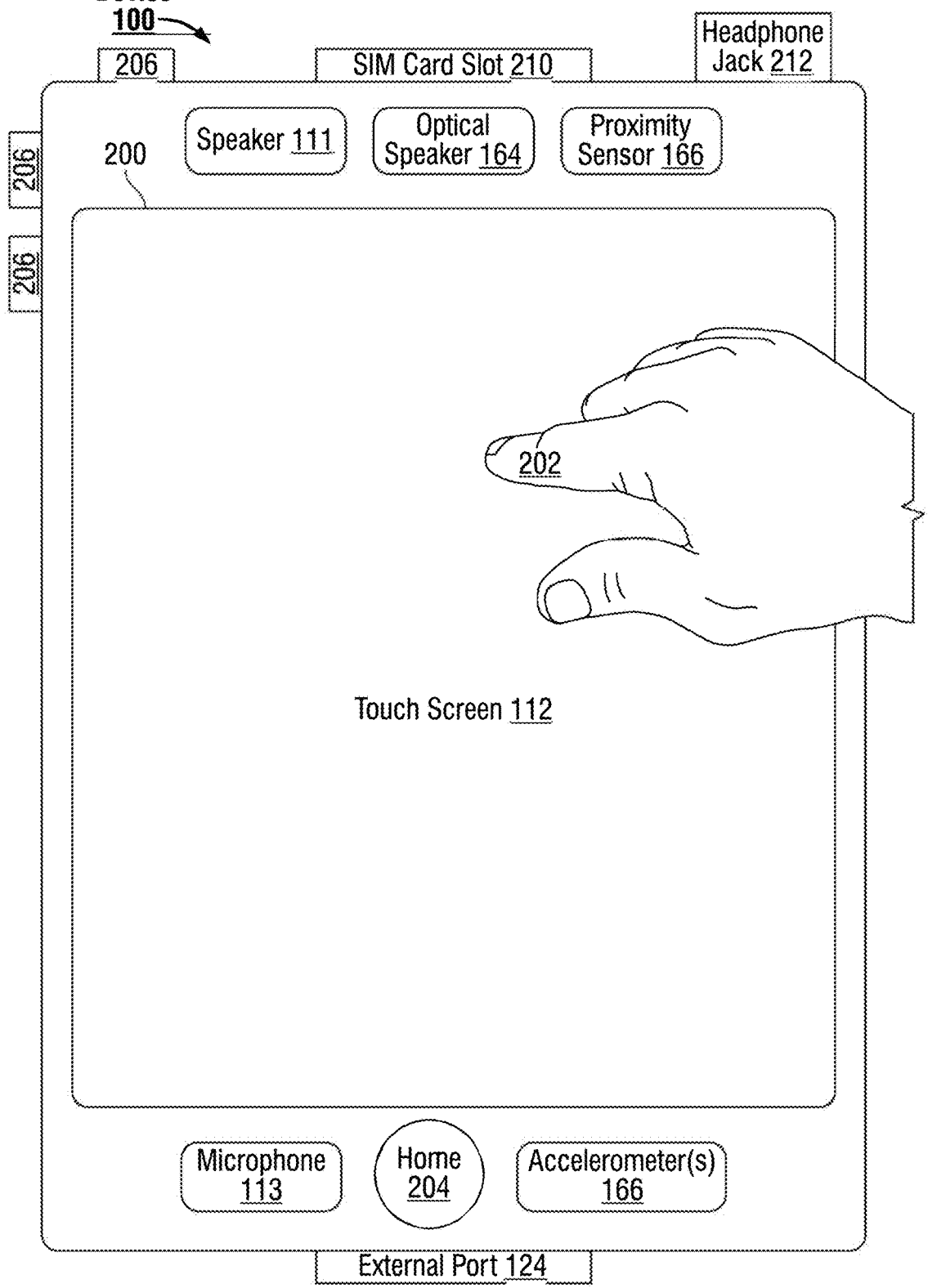
FIG. 5 illustrates a portable multifunction device having a touch screen in accordance with some embodiments.

FIG. 5 illustrates a portable multifunction device 100 having a touch screen 112 in accordance with some embodiments. The touch screen may display one or more graphics within user interface (UI) 200. In this embodiment, as well as others described below, a user may select one or more of the graphics by making contact or touching the graphics, for example, with one or more fingers 202 (not drawn to scale in the FIGURE). In some embodiments, selection of one or more graphics occurs when the user breaks contact with the one or more graphics. In some embodiments, the contact may include a gesture, such as one or more taps, one or more swipes (from left to right, right to left, upward and/or downward) and/or a rolling of a finger (from right to left, left to right, upward and/or downward) that has made contact with the device 100. In some embodiments, inadvertent contact with a graphic may not select the graphic. For example, a swipe gesture that sweeps over an application icon may not select the corresponding application when the gesture corresponding to selection is a tap.

The device 100 may also include one or more physical buttons, such as "home" or menu button 204. As described previously, the menu button 204 may be used to navigate to any application 136 in a set of applications that may be executed on the device 100. Alternatively, in some embodiments, the menu button is implemented as a soft key in a GUI in touch screen 112.

In one embodiment, the device 100 includes a touch screen 112, a menu button 204, a push button 206 for powering the device on/off and locking the device, volume adjustment button(s) 208, a Subscriber Identity Module (SIM) card slot 210, a head set jack 212, and a docking/charging external port 124. The push button 206 may be used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, the device 100 also may accept verbal input for activation or deactivation of some functions through the microphone 113.

Additional embodiments of the present disclosure made advantageous use of (a) light coding technology, (b) three-dimensional sensing using speckle patterns, (c) depth-varying light fields for three dimensional sensing, (d) systems and methods for imaging and image processing for creating an image having blurred and non blurred areas, (e) real-time camera tracking using depth maps, and (f) depth map calculation in a stereo camera system, all as may be applicable to the present disclosure and the advantages thereof.

Light Coding Technology-PrimeSense's depth acquisition was enabled by "light coding" technology. Internet address http://www.i3du.gr/pdf/primesense.pdf provides a disclosure of the operation of light coding technology and here is expressly incorporated by reference in its entirety. The process may code a scene as here presented with near-IR light, light that returns distorted depending upon where things are. The solution then used a standard off-the-shelf CMOS image sensor to read the coded light back from the scene using various algorithms to triangulate and extract the 3D data. The product analyzed scenery in 3 dimensions with software, so that devices could interact with users.

U.S. Pat. No. 8,390,821B2 discloses and claims "Three-dimensional sensing using speckle patterns" for mapping of three-dimensional (3D) objects, and specifically to 3D optical imaging using speckle patterns, and is here expressly incorporated by reference in its entirety. This patent disclosure provides an apparatus for 3D mapping of an object includes an illumination assembly, including a coherent light source and a diffuser, which are arranged to project a primary speckle pattern on the object. A single image capture assembly is arranged to capture images of the primary speckle pattern on the object from a single, fixed location and angle relative to the illumination assembly. A processor is coupled to process the images of the primary speckle pattern captured at the single, fixed angle so as to derive a 3D map of the object.

U.S. Patent Application Publication No. 20080106746 discloses a "Depth-varying light fields for three dimensional sensing" for mapping three-dimensional (3D) objects, and specifically to 3D optical ranging and mapping, and is here expressly incorporated by reference in its entirety. This patent disclosure provides a method for mapping includes projecting onto an object a pattern of multiple spots having respective positions and shapes, such that the positions of the spots in the pattern are uncorrelated, while the shapes share a common characteristic. An image of the spots on the object is captured and processed so as to derive a three-dimensional (3D) map of the object.

U.S. Patent Application Publication No. 20140192238 discloses a "System and Method for Imaging and Image Processing" for creating an image having blurred and non blurred areas using an image capturing device and for creating an image with highlighted differences in an image sequence, and is here expressly incorporated by reference in its entirety. This patent disclosure provides shows for one or more objects of interest from a scene that are selected the calculation of depth information. Additionally, depth information of the scene is calculated. The calculated depth information of the one or more objects is compared with calculated depth information of the scene. Based on the comparison, a blur is applied to an image that includes the scene.

U.S. Pat. No. 9,242,171 discloses a "Real-time camera tracking using depth maps" for tracking the orientation and position of a camera as it moves in an environment, and is here expressly incorporated by reference in its entirety. This patent disclosure provides a real-time camera tracking using depth maps. In an embodiment depth map frames are captured by a mobile depth camera at over 20 frames per second and used to dynamically update in real-time a set of registration parameters which specify how the mobile depth camera has moved. In examples the real-time camera tracking output is used for computer game applications and robotics. In an example, an iterative closest point process is used with projective data association and a point-to-plane error metric in order to compute the updated registration parameters. In an example, a graphics processing unit (GPU) implementation is used to optimize the error metric in real-time. In some embodiments, a dense 3D model of the mobile camera environment is used.

U.S. Pat. No. 5,191,347 discloses a "Pulsed Doppler Radar System" for detecting a target moving at a high speed, and is here expressly incorporated by reference in its entirety. The inventive subject matter there includes a pulsed Doppler radar system comprises a transmitter for generating and transmitting a pulse signal having expanded frequency bandwidth, an antenna apparatus for sending the output of the transmitter to a target and for receiving a signal which was sent by the transmitter and reflected by the target, a receiver for processing the received signal to obtain a complex video signal, a pulse compressing circuit including a pulse Doppler processor responsive to the complex video signal for detecting a relative speed of the target and a storage device for storing a reference signal which includes a compensation factor by which an influence of the Doppler effect is compensated in accordance with the speed of the target. The pulse compressing circuit is operative to correlate the output of the pulse Doppler processor with the reference signal so as to convert the complex video signal to a signal having a narrow pulse width, a detector for performing envelope detection on the narrow pulse width signal, and a display responsive to the output of the detector for displaying a detected target thereon.

U.S. Pat. No. 8,944,681 discloses a "Mobile X-ray Machine with An Anticollision Device," and is here expressly incorporated by reference in its entirety. The inventive subject matter there includes a means for generating a depth map using a stereo camera system to capture two images of an object, determining a difference in blur between the two images at a particular point, and determining a depth for a depth map based on the difference in blur. US patent application publication No. 20170069097 is here expressly incorporated by reference in its entirety. The method includes obtaining a first image of scene from a first image capture unit, the first image having a first depth-of-field (DOF), obtaining a second image of the scene from a second image capture unit, the second image having a second DOF that is different than the first DOF. Each pixel in the second image has a corresponding pixel in the first image. The method also includes generating a plurality of third images, each corresponding to a blurred version of the second image at the each of a plurality of specified depths, generating a plurality of fourth images, each representing a difference between the first image and one or the plurality of third images, and generating a depth map where each pixel in the depth map is based on the pixels in one of plurality of fourth images.

U.S. Patent Application Publication No. 20170069097 discloses a "Depth Map Calculation in a Stereo Camera System," and is here expressly incorporated by reference in its entirety. The disclosure provides a means for generating a depth map using a stereo camera system to capture two images of an object, determining a difference in blur between the two images at a particular point, and determining a depth for a depth map based on the difference in blur. The method includes An X-ray machine is provided. The X-ray machine comprises an X-ray tube; an X-ray detector placed opposite the X-ray tube in a direction of emission of X-rays; and a mobile device on which the X-ray tube and the X-ray detector are mounted, the mobile device comprising a motor capable of causing the automatic movement of the X-ray machine, and an impact-sensing system coupled to the motor in order to control the movement of the mobile device in the event of an impact applied to the X-ray apparatus.

U.S. Pat. No. 6,934,574 discloses a "MRI Scanner and Method for Modular Patient Handling," and is here expressly incorporated by reference in its entirety. An MRI scanner that includes a magnet with poles having substantially vertical pole surfaces and a removable positioner for supporting a patient within a gap in the pole surfaces. A method of positioning a patient within a gap formed by vertical pole surfaces in an MRI scanner. The method includes selecting a first patient positioner and inserting the first patient positioner into the gap between vertical pole surfaces in the MRI scanner.

U.S. Patent Application Publication No. 20140215280 discloses a "CT Scanning System and A Method for Receiving and Transmitting Raw Data Therein," and is here expressly incorporated by reference in its entirety. The patent disclosure provides a means for generating a depth map using a stereo camera system to capture two images of an object, determining a difference in blur between the two images at a particular point, and determining a depth for a depth map based on the difference in blur. The disclosure includes transmitting raw data by a data acquisition system in a CT scanning system, wherein the CT scanning system comprises a rotational part of a gantry with at least one raw data backup memory, and wherein the data acquisition system is configured to adopt the at least one backup memory for storing a backup of the raw data. The method comprising: generating the raw data as scanned; storing generated raw data in the at least one backup memory; transmitting the raw data to an operation console in the CT scanning system; and repeating generating, storing, and transmitting of the raw data in the case of an unfinished scan, until the unfinished scan is finished.

International Patent Cooperation Treaty (PCT) Application Publication No. WO 2009088408 A1 discloses a "Discovery Tool with Integrated Microfluidic Biomarker Optical Detection Array Device and Methods for Use," and is here expressly incorporated by reference in its entirety. This disclosure relates to the fields of microchips with microfluidic optical chambers with enhanced Raman surfaces for multiplexed optical spectroscopy. Embodiments of the present invention allow for ultra small sample volume, as well as high detection speed and throughput, as compared to conventional cuvettes or devices used in optical spectroscopy. Particular embodiments relate to scientific and medical research, the diagnosis of diseases such as cancer, cardiovascular disease, diabetes, etc., and specifically to the detection of biomarkers and determination of protein activity with relevant scientific and medical applications.

The present disclosure, using all of the subject herein presented and incorporated by reference, provides for the collection of information from a mobile device with transparent display screen, and mobile device with dual non-transparent screen facing front and rear (rear screen may be E-type reader) with utilization software, GPS/Location, date and time data and all sensors to include camera base 3D and or 3D sensor. Such functions and benefits include, and are not limited to (a) measuring the mobile device's distance from the advertisement viewers; (b) facial reaction as advertisement is being displayed; (c) eye position toward the advertisement while being displayed; (d) Body/clothing features to include size and mass of audience; (e) audience gender; (f) number of audience within sensor's area limits; (g) type of clothing audience are wearing; (h) surrounding environment information; (i) identify color; as well as (j) any other information sensors to include 3D sensor data may be able to collect with mobile device.

In conjunction with the data collection and functions as provided above, the disclosed subject matter discloses and expressly incorporates features and functions including a mobile software application to adjust, improve AR/MR images. These functions may include (a) refining an advertisement for a target audience; (b) enhancing advertisement for target audience; (c) adjusting the size of the advertisement or image; (d) enhancing the content of advertisement; (e) aligning the subject and generated image through transparent display screen; (f) changing the size of the generated advertisement, AR, MR image; (g) changing the duration of advertisement or image content; (h) adjusting the depth and angle of AR, MR image; (i) correcting the angle of view for parallax image; (j) aligning users viewing angle to display image AR, MR image color intensity to include translucent images; as well as (k) any other modifications to advertisement, as needed to increase improve visual and subject content.

The present disclosure, using all of the subject herein presented and incorporated by reference, provides for the collection of information from a mobile device with transparent display screen, and mobile device with dual non-transparent screen facing front and rear (rear screen may be E-type reader) with utilization software, GPS/Location, date and time data and all sensors to include camera base 3D and or 3D sensor. Such functions and benefits include, and are not limited to (a) measuring the mobile device's distance from the advertisement viewers; (b) facial reaction as advertisement is being displayed; (c) eye position toward the advertisement while being displayed; (d) Body/clothing features to include size and mass of audience; (e) audience gender; (f) number of audience within sensor's area limits; (g) type of clothing audience are wearing; (h) surrounding environment information; (i) identify color; as well as (j) any other information sensors to include 3D sensor data may be able to collect with mobile device.

In conjunction with the data collection and functions as provided above, the disclosed subject matter discloses and expressly incorporates features and functions including a mobile software application to adjust, improve AR/MR images. These functions may include (a) refining an advertisement for a target audience; (b) enhancing advertisement for target audience; (c) adjusting the size of the advertisement or image; (d) enhancing the content of advertisement; (e) aligning the subject and generated image through transparent display screen; (f) changing the size of the generated advertisement, AR, MR image; (g) changing the duration of advertisement or image content; (h) adjusting the depth and angle of AR, MR image; (i) correcting the angle of view for parallax image; (j) aligning users viewing angle to display image AR, MR image color intensity to include translucent images; as well as (k) any other modifications to advertisement, as needed to increase improve visual and subject content.

With use of software and data collected such as GPS/location, time and date, on mobile device with transparent display screen, information/data collected from 3D sensor and or 3D camera sensor may include eyes, face position alignment toward the image and to the image being displayed on transparent display screen, object features to include size, surrounding environment, and any other information 3D sensor may be able to collect within mobile device's viewable area and or senor's area limit. With collected information, software apps may utilize to adjust depth, size, color, texture (shown in translucent parallax image), image intensity, angle of view of parallax images, translucency, subject content and any other information deemed important to application to improve Augmented Reality (AR), Mix Reality (MR) or Photo applications and for immediate or future application, while mobile device is in use with acknowledgement by device user.

In addition, with utilization front and rear 3D sensor on a mobile device, may be utilized align viewing angle of AR/MR (MR for blocking out unwanted objects) images with background viewed on transparent screen.

With improvement in sensor and software technology for mobile device, smart mobile devices can calculate color and texture (3D sensor) to match the pattern. For fine detail, device user may adjust or fine tune final selection. At present time, trained human eyes comparison cannot be matched for non-commercial applications. For matching or compare color or texture viewed through transparent display screen, texture may be shown in translucent for top layer and solid or translucent color as bottom layer of parallax image. For fluid or color in atmosphere space, color may be shown in translucent color.

Figure 6:
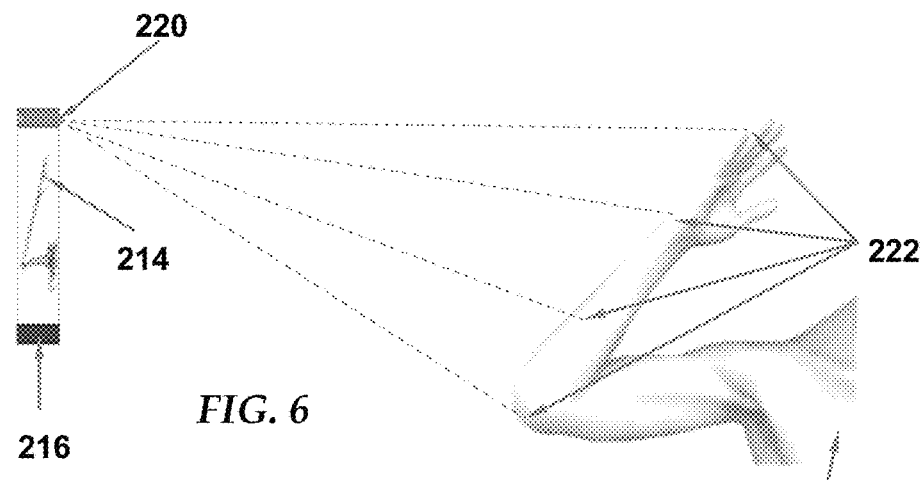
FIGS. 6 through 8 illustrates aspects of using the presently disclosed method and system for physical correlation with images through a portable multifunction device.
Figure 7:
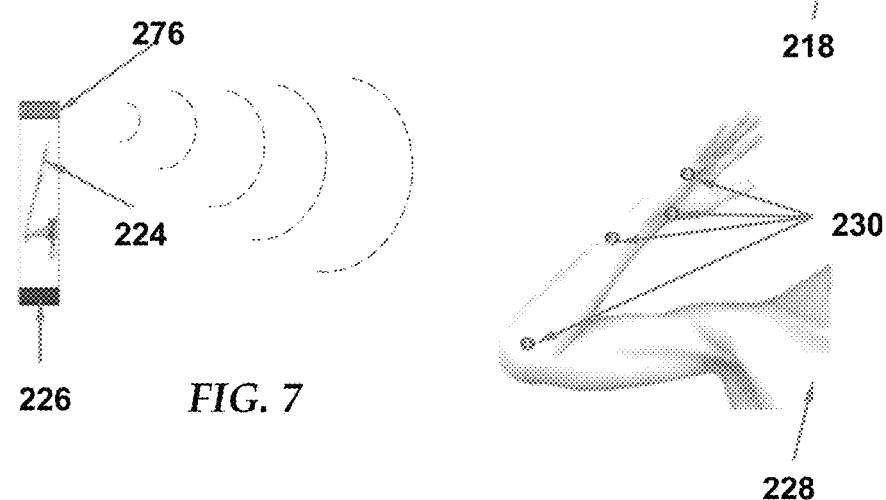

FIGS. 6 and 7 present the image of mobile device with transparent display screen 216 being utilized for AR color sample 220 and AR texture image sample 222 comparison of object 214 seen through transparent display screen. Built-in front 3D sensor 218 may be utilized to align viewing angle of AR and object being compared through transparent display screen.

Figure 8:
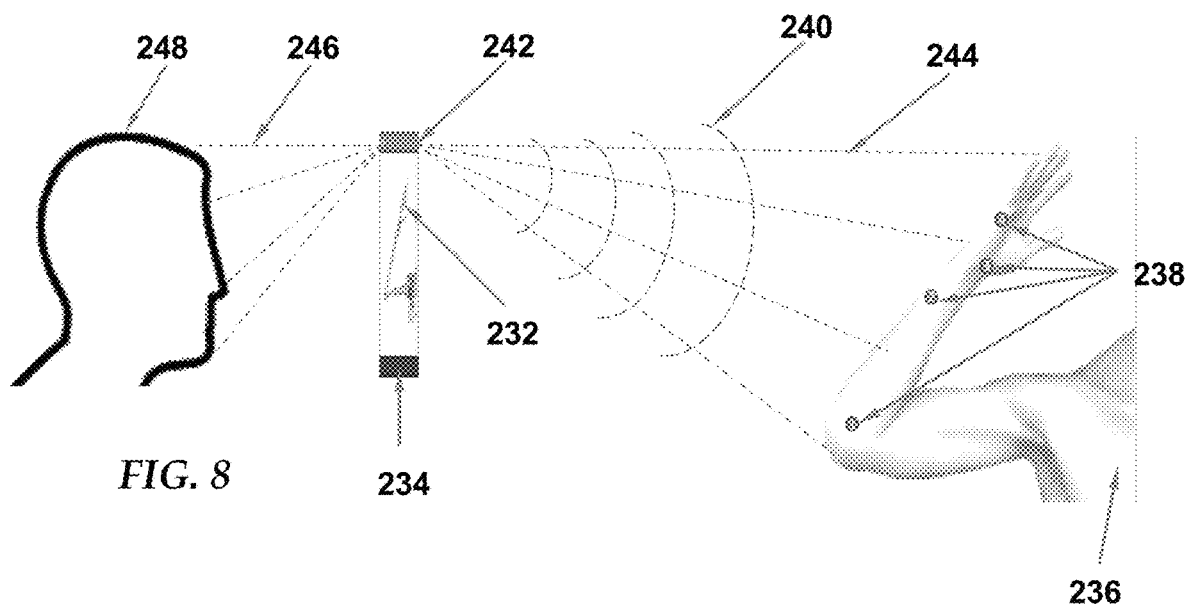

FIG. 8 show images of a mobile device user 224 viewing 226 an object 234 through mobile device transparent screen 232 for comparing AR image, color and texture 230. Front 3D sensor 236 focused on multiple points on user and rear 3D sensor 228 focused on multiple points of an object being to align AR image.

Figure 9:
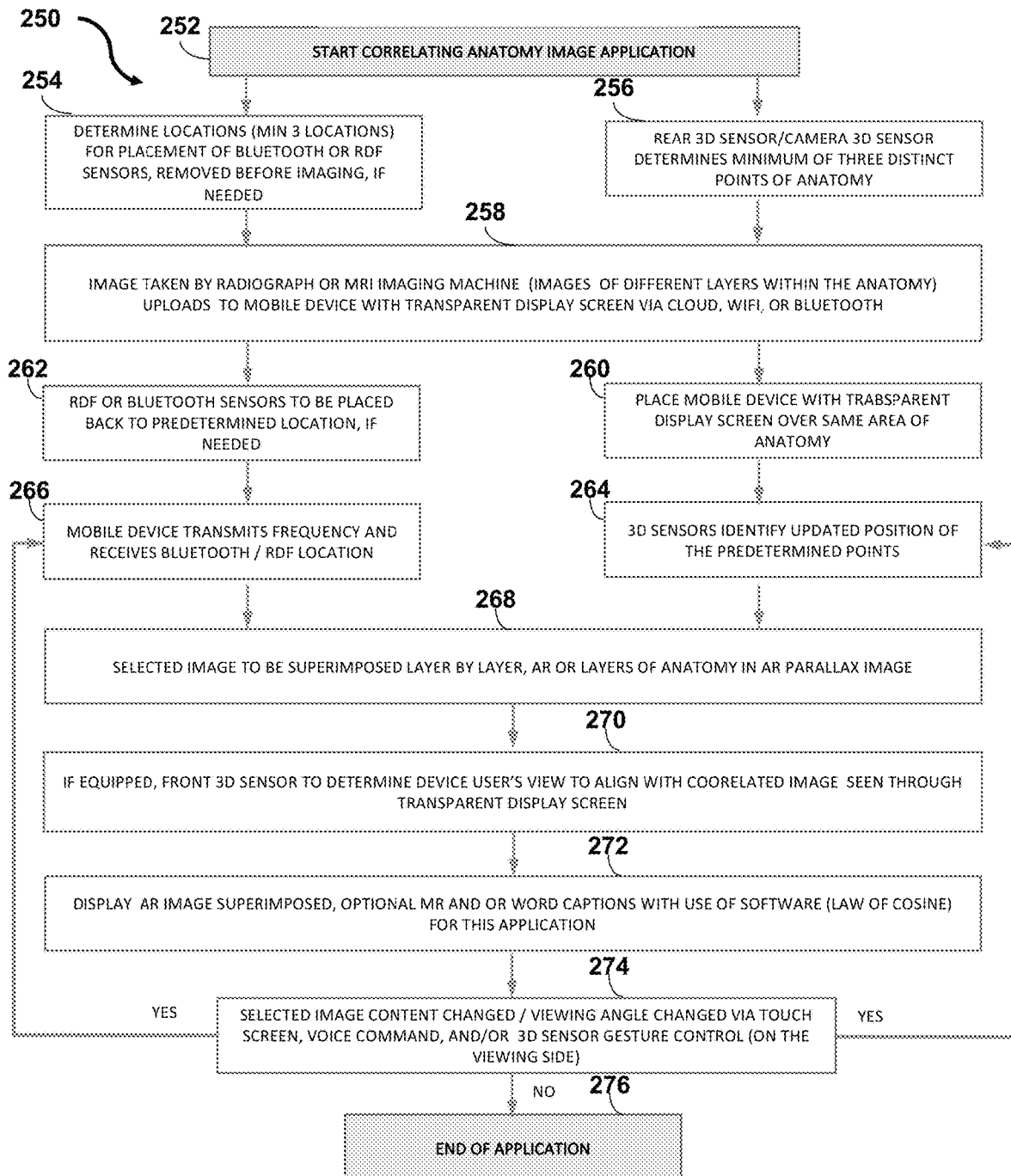
FIG. 9 illustrates a flowchart of a process for correlating anatomy image according to the teachings of the present disclosure.

FIG. 9 provides flow chart 250, which is an example consisting of using software, GPS/location, time and data, on mobile device with transparent display, information from 3D sensor, camera sensors include texture of object being compared to, color, and any other information needed. With collected information, sample of matching texture and color will be displayed for device user's final approval. Device user may manually choose matching color and texture. This process can be modified or restructured as needed according to different operating systems and capabilities of different mobile devices.

Process 250 of FIG. 9 begins at step 252 which start correlating anatomy image application. At step 254, the pocess determine locations (min 3 locations) for placement of bluetooth or rdf sensors, removed before imaging, if needed. At step 256, the rear 3D sensor/camera 3D sensor determines minimum of three distinct points of anatomy. At step 258, an image is taken by radiograph or MRI imaging machine (images of different layers within the anatomy) uploads to mobile device with transparent display screen via cloud, Wi-Fi, or Bluetooth.

Process 250 places mobile device with transparent display screen over same area of anatomy, at step 260. At step 262, RDF or Bluetooth sensors are to be placed back to predetermined location, if needed. At step 264, 3D sensors identify updated position of the predetermined points. The mobile device transmits frequency and receives Bluetooth/RDF location, at step 266. At step 268, the selected image to be superimposed layer by layer, AR or layers of anatomy in AR parallax image. At step 270, if the mobile device is so equipped, a front 3D sensor may determine device user's view to align with correlated image seen through transparent display screen. The display for the AR image superimposed, optional MR and/or word captions with use of software (law of cosine) for this application, at step 272. At step 274, selected image content may be changed and/or the viewing angle changed via touch screen, voice command, and/or 3D sensor gesture control (on the viewing side). The application terminates at step 276.

With utilization of software and 3D sensor to include camera sensors, images produced by using radiograph or MRI image machine, hand held cardiovascular scanner with Doppler technology and other medical imaging devices, images are displayed on mobile device on conventional LED/OLED non-transparent and or transparent display screen as augmented reality (AR), mixed reality (MR) superimposed on to actual part of anatomy. The mobile device with transparent display screen may focus on multiple points of anatomy while viewing angle is changing depending user's viewing angle. Device user's view are tracked using a combination of the cameras, projections and computer vision algorithms to calculate the positions of the eyes and or face position at the gaze point on transparent display screen. Using software and 3D sensor's recorded position information, a minimum of three or more points (Law of Cosine) can be used to locate the updated position of the superimposed radiograph or MRI image on to the actual anatomy. Multiple RDF and/or Bluetooth markers may work in conjunction with 3D sensors for improved accuracy.

With identification of multiple benchmark location either with 3D camera/sensor or use with or without conjunction with multiple RF/Bluetooth/NFC tags is to used with Law of Cosine, software and algorithm is to create 3D mapping of image taken before, during and or after imaging with various medical imaging device.

Certain medical imaging devices like hand held cardiovascular sensor with Doppler technology which may be hard to distinguish depth of cardiovascular image displayed on the skin, may benefit from incorporating 3D camera/sensor use to map and record cardiovascular image which exported and incorporated with other imaging device to create improved combined imaging for improved study of anatomy.

Figure 10:
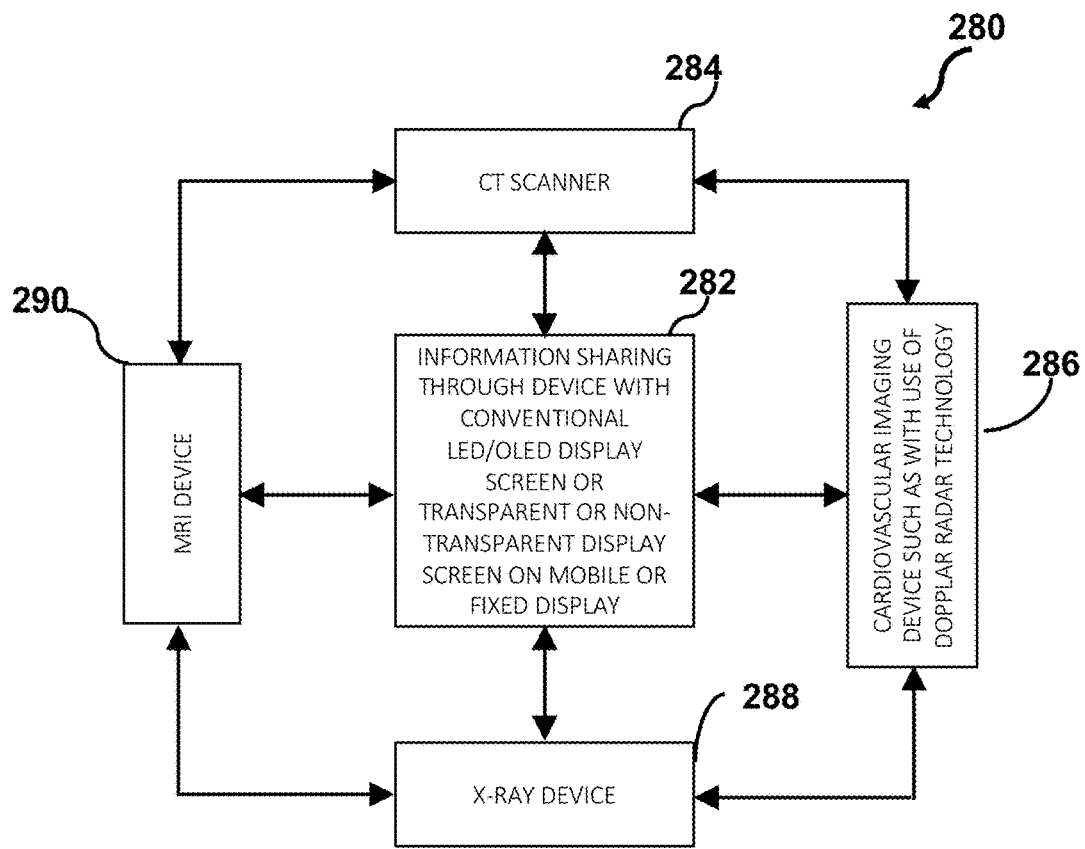
FIG. 10 depicts a process for coordinating the inputs and outputs of a method consistent with the present teachings for use with a CT scanner, an MRI device, X-ray device, cardiovascular imaging device, and an LED/OLED display screen or transparent or non-transparent display screen on mobile or fixed display.

FIG. 10 depicts a process for coordinating the inputs and outputs of a method consistent with the present teachings for use with a CT scanner, an MRI device, X-ray device, cardiovascular imaging device, and an LED/OLED display screen or transparent or non-transparent display screen on mobile or fixed display.

"Along with benchmark locations/reference points, with use of software, algorithms and law of cosine use for correlate radiograph images display on transparent t display or non transparent display screen over scanned, radiograph images imposed and correlated on to area of radiograph area to enhanced image displayed all images seen over same area. With though mobile device with 3D sensor, 3D optical sensor and or with RF, Bluetooth/NFC sensor on transparent display or conventional non transparent display screen viewed though camera image.

Correlation of anatomy/images to include industrial material, such as welded x-ray joints material such as metal beams, tubing, also bonded material, etc., displayed onto display screen, transformer non-transparent, on a mobile device. The material is scanned for benchmark points using 3D scanner/3D optical/Bluetooth, RF, NFC. After material radiography/x-rayed and imaged, the radiographed image is seen through transparent screen or camera viewed through conventional displayed screen.

Regarding 3D sensor, as we talked about use of future iPad/tablet/mobile device with conventional screen with 3D sensor. Prior to x-Ray/MRI/medical imaging, scan the area with 3D sensor on the mobile device. Alternatively, scanning may use a separate 3D sensor or 3D sensor built into medical imaging device for coordinate control/benchmark location. After the x-ray/MRI/medical imaging, image and coordination/benchmark location is transfer to mobile device with 3D sensor to correlate x-ray/MRI/medical imaging on to conventional screen on a mobile device with 3D sensor.

Along with visual markers as point of base identifications, RF, NFC and or Bluetooth tags may also be utilized point of base markers for identification, which may be removed during radiograph imaging and place back in same location for mobile device to correlate x-ray images with utilization of built in RF, NFC and or Bluetooth sensors in a mobile device. Which may be incorporated with 3D sensors or may operate alone as point of reference markers for correlating x-ray/MRI and other images on a mobile device.

Figure 11:
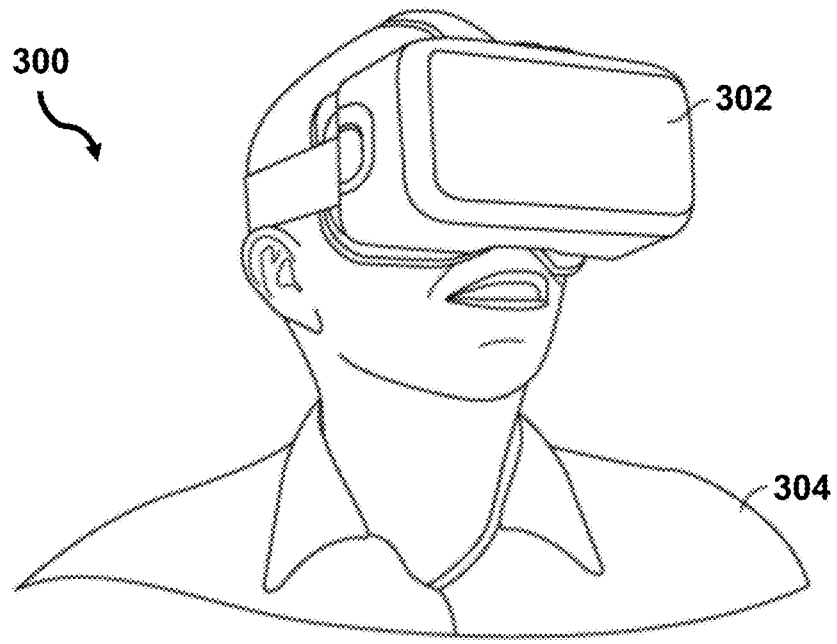
FIG. 11 depicts a user wearing a virtual reality or augmented reality head mounted display that may employ the teachings of the present disclosure.

FIG. 11 depicts a scenario 300 wherein a virtual reality or augmented reality head mounted display 302 demonstrates use for the teachings of the present disclosure. FIG. 11 depicts user 304 employing a virtual reality or augmented reality head mounted display that may employ the teachings of the present disclosure. Head mounted display (HMD) 302 for viewing a virtual reality environment may occur by a user 304 wearing the device to begin a virtual reality experience. So, here a wearable device for employing the present teachings includes mobile device and x-ray for welding inspection to be used for commercial applications, e.g., pipe and welded joints.

A technical aspect of the present disclosure includes the ability to align the sensors so with the number for if there are multiple surgeries and we have a parallax image. There is the date the ability to go deeper with a hand gesture and to understand how the alignment of the sensors occurs for the x-ray image with the optical image in with the display.

In summary, the present disclosure provides a method, system, and integrated medical imaging system for forming a correlated view of human or other animal anatomy using at least one transparent display screen associated with an electronic mobile device. The view relates an optical view with other electromagnetic spectrum images with a non-optical electromagnetic image of selected portions of human or other animal anatomy. The disclosure associates at least three visible position markers with selected positions of a predetermined portion of human or other animal anatomy. The at least three visible position markers provide a predetermined measure of opacity for selected non-optical electromagnetic frequencies. The method and system imaging the predetermined portion of human or other animal anatomy using at least a subset of selected non-optical electromagnetic frequencies using an electromagnetic imaging device optical electromagnetic image of said predetermined portion of human or other animal anatomy. The at least three visible position markers and at least three visible position markers exhibit at least partial opacity for at least one of said subset of selected non-optical electromagnetic frequencies. The method and system forming an optical view of the predetermined portion of human or other animal anatomy through at least a portion of a transparent display screen associated with said electronic mobile device. The disclosure forms a correlated view of the predetermined portion of human or other animal anatomy by relating said at least one non-optical electromagnetic image of the at least three visible position markers with a visual image of said at least three visible position markers. The view correlates the size and dimensions of the optical view and non-optical electromagnetic image of the predetermined portion of human or other animal anatomy.

The detailed description set forth herein in connection with the appended drawings is intended as a description of exemplary embodiments in which the presently disclosed subject matter may be practiced. The term "exemplary" used throughout this description means "serving as an example, instance, or illustration," and should not necessarily be construed as preferred or advantageous over other embodiments.

This detailed description of illustrative embodiments includes specific details for providing a thorough understanding of the presently disclosed subject matter. However, it will be apparent to those skilled in the art that the presently disclosed subject matter may be practiced without these specific details. In some instances, well-known structures and devices are shown in block diagram form in order to avoid obscuring the concepts of the presently disclosed method and system.

The foregoing description of embodiments is provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter set forth in the claims is not intended to be limited to the embodiments shown herein, but is to be accorded the widest scope consistent with the principles and novel features disclosed herein. It is contemplated that additional embodiments are within the spirit and true scope of the disclosed subject matter.

What is claimed is:

1. A method for forming a correlated view of human or other animal anatomy using at least one transparent display screen associated with an electronic mobile device, said view relating an optical view with other electromagnetic spectrum images with at least one non-optical electromagnetic image of selected portions of human or other animal anatomy, the method comprising the steps of: associating at least three visible position markers with selected positions of a predetermined portion of human or other animal anatomy, said at least three visible position markers comprising a predetermined measure of opacity for selected non-optical electromagnetic frequencies;

imaging said predetermined portion of human or other animal anatomy using at least a subset of said selected non-optical electromagnetic frequencies using an electromagnetic imaging device for forming the at least one non-optical electromagnetic image of said predetermined portion of human or other animal anatomy, including said at least three visible position markers and further wherein said at least three visible position markers exhibit at least partial opacity for at least one of said subset of selected non-optical electromagnetic frequencies;

forming the optical view of said predetermined portion of human or other animal anatomy through at least a portion of the transparent display screen associated with said electronic mobile device;

forming the correlated view of said predetermined portion of human or other animal anatomy by relating said at least one non-optical electromagnetic image of said at least three visible position markers with a visual image of said at least three visible position markers, said correlated view correlating the size and dimensions of said optical view and said at least one non-optical electromagnetic image of said predetermined portion of human or other animal anatomy; and further correlating said optical view formed of said predetermined portion of human or other animal anatomy with at least a set of image information from the group consisting of a CT scanner, an MRI device, an X-ray device, and a cardiovascular imaging device using doppler radar sensing technique for displaying on said transparent display screen associated with said electronic mobile device.

2. The method of claim 1, wherein said non-optical electromagnetic frequencies comprise X-ray frequencies and said at least one non-optical electromagnetic image comprises an X-ray image.

3. The method of claim 1, wherein said non-optical electromagnetic frequencies comprise magnetic resonance frequencies and said at least one non-optical electromagnetic image comprises a magnetic resonance image.

4. The method of claim 1, wherein said predetermined portion of human or other animal anatomy comprises flesh tissue.

5. The method of claim 1, wherein said predetermined portion of human or other animal anatomy comprises skeletal anatomy.

6. The method of claim 1, wherein said at least three visible position markers exhibit at least partial opacity to a plurality of non-optical electromagnetic frequencies.

7. The method of claim 1, wherein said at least three visible position markers further comprise electromagnetic transmitters for transmitting position signals from said selected positions of said predetermined portion of said human or other animal anatomy.

8. A system for forming a correlated view of human or other animal anatomy using at least one transparent display screen associated with an electronic mobile device, said view relating an optical view with other electromagnetic spectrum images with a with at least one non-optical electromagnetic image of selected portions of human or other animal anatomy, the system comprising:

computer executable instructions and circuitry for associating at least three visible position markers with selected positions of a predetermined portion of human or other animal anatomy, said at least three visible position markers comprising a predetermined measure of opacity for selected non-optical electromagnetic frequencies;

computer executable instructions and circuitry for imaging said predetermined portion of human or other animal anatomy using at least a subset of said selected non-optical electromagnetic frequencies using an electromagnetic imaging device for forming the at least one non-optical electromagnetic image of said predetermined portion of human or other animal anatomy, including said at least three visible position markers and further wherein said at least three visible position markers exhibit at least partial opacity for at least one of said subset of selected non-optical electromagnetic frequencies;

computer executable instructions and circuitry for forming the optical view of said predetermined portion of human or other animal anatomy through at least a portion of the transparent display screen associated with said electronic mobile device;

computer executable instructions and circuitry for forming the correlated view of said predetermined portion of human or other animal anatomy by relating said at least one non-optical electromagnetic image of said at least three visible position markers with a visual image of said at least three visible position markers, said correlated view correlating the size and dimensions of said optical view and said at least one non-optical electromagnetic image of said predetermined portion of human or other animal anatomy; and computer executable instructions and circuitry for further correlating said optical view formed of said predetermined portion of human or other animal anatomy with at least a set of image information from the group consisting of a CT scanner, an MRI device, an X-ray device, and a cardiovascular imaging device using doppler radar sensing technique for displaying on said transparent display screen associated with said electronic mobile device.

9. The system of claim 8, wherein said non-optical electromagnetic frequencies comprise X-ray frequencies and said at least one non-optical electromagnetic image comprises an X-ray image.

10. The system of claim 8, wherein said non-optical electromagnetic frequencies comprise magnetic resonance frequencies and said at least one non-optical electromagnetic image comprises a magnetic resonance image.

11. The system of claim 8, wherein said predetermined portion of human or other animal anatomy comprises flesh tissue.

12. The system of claim 8, wherein said at least three visible position markers further comprise RF transmitters for transmitting position signals from said selected positions of said predetermined portion of said human or other animal anatomy.

13. The system of claim 8, wherein said at least three visible position markers further comprise Bluetooth transmitters for transmitting position signals from said selected positions of said predetermined portion of said human or other animal anatomy.

14. The system of claim 8, further comprises computer executable instructions and circuitry for displaying said correlated view of said predetermined portion of human or other animal anatomy as a parallax image for enhancing visual effects associating with said correlated view.

15. The system of claim 8, wherein said predetermined portion of human or other animal anatomy comprises a predetermined internal organ tissue.

16. A method for forming a correlated view of human or other animal anatomy using at least one transparent display screen or non-transparent display screen associated with an electronic mobile device, said view relating an optical view with other electromagnetic spectrum images with at least one non-optical electromagnetic image of selected portions of human or other animal anatomy, the method comprising the steps of:

associating at least three visible position markers with or without radio frequency (RF)/near-field-communication (NFC) or Bluetooth marking sensors with selected positions of a predetermined portion of human or other animal anatomy, said at least three visible position markers comprising a predetermined measure of opacity for selected non-optical electromagnetic frequencies;

imaging said predetermined portion of human or other animal anatomy using at least a subset of said selected non-optical electromagnetic frequencies using an electromagnetic imaging device for forming the at least one non-optical electromagnetic image of said predetermined portion of human or other animal anatomy, including said at least three visible position markers with or without RF/NFC or Bluetooth marking sensors and further wherein said at least three visible position markers exhibit at least partial opacity for at least one of said subset of selected non-optical electromagnetic frequencies;

forming the optical view of said predetermined portion of human or other animal anatomy through at least a portion of the transparent display screen associated with said electronic mobile device;

forming the correlated view of said predetermined portion of human or other animal anatomy by relating said at least one non-optical electromagnetic image of said at least three visible position markers with a visual image of said at least three visible position markers, said correlated view correlating the size and dimensions of said optical view and said at least one non-optical electromagnetic image of said predetermined portion of human or other animal anatomy and further enhancing the transparent display screen through collection of various information for feedback with utilization of sensors including three-dimensional (3D) camera and/or 3D sensor.

17. The method of claim 16, wherein said non-optical electromagnetic frequencies comprise X-ray frequencies and said at least one non-optical electromagnetic image comprises an X-ray image.

18. The method of claim 16, wherein said non-optical electromagnetic frequencies comprise magnetic resonance frequencies and said at least one non-optical electromagnetic image comprises a magnetic resonance image.

19. The method of claim 16, wherein said predetermined portion of human or other animal anatomy comprises flesh tissue.

20. The method of claim 16, wherein said predetermined portion of human or other animal anatomy comprises skeletal anatomy.

21. The method of claim 16, wherein said at least three visible position markers exhibit at least partial opacity to a plurality of non-optical electromagnetic frequencies.

22. The method of claim 16, wherein said at least three visible position markers further comprise electromagnetic transmitters for transmitting position signals from said selected positions of said predetermined portion of said human or other animal anatomy.

23. A system for forming a correlated view of human or other animal anatomy using at least one transparent display screen associated with an electronic mobile device, said view relating an optical view with other electromagnetic spectrum images with at least one non-optical electromagnetic image of selected portions of human or other animal anatomy, the system comprising:

computer executable instructions and circuitry for associating at least three visible position markers with or without radio frequency (RF)/near-field-communication (NFC) or Bluetooth marking sensors with selected positions of a predetermined portion of human or other animal anatomy, said at least three visible position markers comprising a predetermined measure of opacity for selected non-optical electromagnetic frequencies;

computer executable instructions and circuitry for imaging said predetermined portion of human or other animal anatomy using at least a subset of said selected non-optical electromagnetic frequencies using an electromagnetic imaging device for forming the at least one non-optical electromagnetic image of said predetermined portion of human or other animal anatomy, including said at least three visible position markers and wherein said at least three visible position markers exhibit at least partial opacity for at least one of said subset of selected non-optical electromagnetic frequencies computer executable instructions and circuitry for forming the optical view of said predetermined portion of human or other animal anatomy through at least a portion of the transparent display screen associated with said electronic mobile device computer executable instructions and circuitry for forming the correlated view of said predetermined portion of human or other animal anatomy by relating said at least one non-optical electromagnetic image of said at least three visible position markers with a visual image of said at least three visible position markers, said correlated view correlating the size and dimensions of said optical view and said at least one non-optical electromagnetic image of said predetermined portion of human or another animal anatomy; and circuitry and instructions associated with the mobile device for further enhancing the transparent display screen through collection of various information for feedback with utilization of sensors including three-dimensional (3D) camera and/or 3D sensor.

24. The system of claim 23, wherein said non-optical electromagnetic frequencies comprise X-ray frequencies and said at least one non-optical electromagnetic image comprises an X-ray image.

25. The system of claim 23, wherein said non-optical electromagnetic frequencies comprise magnetic resonance frequencies and said at least one non-optical electromagnetic image comprises a magnetic resonance image.

26. The system of claim 23, wherein said predetermined portion of human or other animal anatomy comprises flesh tissue.

27. The system of claim 23, wherein said at least three visible position markers further comprise RF/NFC transmitters for transmitting position signals from said selected positions of said predetermined portion of said human or other animal anatomy.

28. The system of claim 23, wherein said at least three visible position markers further comprise RF/NFC or Bluetooth transmitters for transmitting position signals from said selected positions of said predetermined portion of said human or other animal anatomy.

29. The system of claim 23, wherein the system displays said correlated view of said predetermined portion of human or other animal anatomy as a parallax image for enhancing visual effects associating with said correlated view.

30. The system of claim 23, wherein said predetermined portion of human or other animal anatomy comprises a predetermined internal organ tissue.

31. The system of claim 23, wherein said predetermined portion of human or other animal anatomy comprises skeletal anatomy.

* * * * *